US011571434B2

(12) United States Patent
Grossi et al.

(10) Patent No.: US 11,571,434 B2
(45) Date of Patent: *Feb. 7, 2023

(54) CONCENTRATED LIQUID PHARMACEUTICAL FORMULATIONS OF FUROSEMIDE

(71) Applicant: scPharmaceuticals Inc., Burlington, MA (US)

(72) Inventors: Alfredo Grossi, Stoneham, MA (US); Britt Kostraba, Sandown, NH (US); Olatokumbo O. Luca Ogunleye, Tewksbury, MA (US); Shannon Terry, Somerville, MA (US); Franciscus Koppenhagen, Salem, NH (US)

(73) Assignee: scPharmaceuticals Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,041

(22) Filed: Aug. 2, 2022

(65) Prior Publication Data

US 2022/0378806 A1 Dec. 1, 2022

Related U.S. Application Data

(63) Continuation of application No. 17/675,043, filed on Feb. 18, 2022, which is a continuation of application No. 17/426,765, filed as application No. PCT/US2020/015799 on Jan. 30, 2020.

(60) Provisional application No. 62/799,215, filed on Jan. 31, 2019.

(51) Int. Cl.
| | |
|---|---|
| *A61K 31/635* | (2006.01) |
| *A61K 47/10* | (2017.01) |
| *A61K 47/18* | (2017.01) |
| *A61K 47/32* | (2006.01) |
| *A61M 5/142* | (2006.01) |

(52) U.S. Cl.
CPC ............ *A61K 31/635* (2013.01); *A61K 47/10* (2013.01); *A61K 47/18* (2013.01); *A61K 47/32* (2013.01); *A61M 5/14248* (2013.01)

(58) Field of Classification Search
CPC ...... A61K 31/635; A61K 47/10; A61K 47/18; A61K 47/32; A61M 5/14248
See application file for complete search history.

(56) References Cited

U.S. PATENT DOCUMENTS

| | | | |
|---|---|---|---|
| 4,663,348 A | 5/1987 | Chafetz et al. | |
| 4,698,361 A | 10/1987 | Di Schiena | |
| 4,861,786 A | 8/1989 | Demmer et al. | |
| 5,633,240 A | 5/1997 | Ranade | |
| 5,814,623 A | 9/1998 | Ranade | |
| 8,282,366 B2 | 10/2012 | Hilber et al. | |
| 8,372,809 B2 | 2/2013 | Unemori et al. | |
| 8,414,532 B2 | 4/2013 | Brandt et al. | |
| 9,884,039 B2 | 2/2018 | Michaels et al. | |
| 10,272,064 B2 | 4/2019 | Michaels et al. | |
| 2008/0076828 A1 | 3/2008 | Dalton et al. | |
| 2009/0233951 A1 | 9/2009 | Somberg et al. | |
| 2011/0060280 A1 | 3/2011 | Caffey et al. | |
| 2012/0077829 A1 | 3/2012 | Somberg et al. | |
| 2013/0252932 A1 | 9/2013 | Seward | |
| 2016/0051507 A1 | 2/2016 | Michaels et al. | |
| 2018/0028665 A1 | 2/2018 | Bova et al. | |
| 2018/0303790 A1 | 10/2018 | Michaels et al. | |
| 2022/0168323 A1 | 6/2022 | Grossi et al. | |

FOREIGN PATENT DOCUMENTS

| | | |
|---|---|---|
| EP | 0801950 A1 | 10/1997 |
| EP | 1078636 A1 | 2/2001 |
| JP | S625975 A | 1/1987 |
| JP | 2011520918 A | 7/2011 |
| WO | WO-1992/21769 A1 | 12/1992 |
| WO | WO-1996/06615 A1 | 3/1996 |
| WO | WO-2009/140659 A2 | 11/2009 |
| WO | WO-2010/030667 A2 | 3/2010 |
| WO | WO-2014/165660 A1 | 10/2014 |
| WO | WO-2020/120482 A1 | 6/2020 |
| WO | WO-2020/141224 A1 | 7/2020 |
| WO | WO-2020/141226 A1 | 7/2020 |

OTHER PUBLICATIONS

U.S. Appl. No. 17/426,765, Concentrated Liquid Pharmaceutical Formulations of Furosemide and Methods of Administering the Same, filed Jul. 29, 2021, Published, US 2022-0096500 Published on Mar. 31, 2022.
U.S. Appl. No. 17/675,043, Concentrated Liquid Pharmaceutical Formulations of Furosemide, filed Feb. 18, 2022 Published, US 2022-0168323 Published on Jun. 2, 2022.
Al-Obaid et al., "Analytical Profile of Furosemide," Analytical Profiles of Drug Substances, 18:153-193(1990).
American Regent, Inc., Furosemide Injection, USP, Product Insert, 16 pages (Feb. 2014).
Anonymous, "Benzyl Alcohol", "Handbook of Pharmaceutical Excipients", Jan. 1, 2006 (Jan. 1, 2006), XP055682028, pp. 69-71.
Aulton M.E., Aulton's Pharmaceutics: The Design and Medicines, Churchill Livingstone, 3rd Ed., (Dec. 31, 2007), Table 24.4.
Beringer et al., Parenteral Preparations—Overview of Unique Characteristics of Parenteral Dosage Forms, Added Substances, Route of Administration, Remington: The Science and Practice of Pharmacy, 21st Edition, Lippincott Williams &Wilkins, 2005, pp. 802-805.
Bundgaard et al., "Photodegradation and hydrolysis of furosemide and furosemide esters in aqueous solutions," International Journal of Pharmaceutics, 42:217-224 (1988).

(Continued)

*Primary Examiner* — Robert A Wax
*Assistant Examiner* — Quanglong N Truong
(74) *Attorney, Agent, or Firm* — Goodwin Procter LLP

(57) ABSTRACT

Disclosed herein, in part, are liquid pharmaceutical formulations comprising furosemide or a pharmaceutically acceptable salt thereof, one or more pharmaceutically acceptable excipients, and a pharmaceutically acceptable buffer. Methods of treating congestion, edema, fluid overload, or hypertension in a patient in need thereof are also provided.

20 Claims, No Drawings

(56) References Cited

OTHER PUBLICATIONS

Cruz et al., "Kinetics and Mechanism of Hydrolysis of Furosemide," International Journal of Pharmaceutics, 2:275-281 (1979).
Devarakonda et al., "Effect of pH on the solubility and release of furosemide from polyamidoamine (PAMAM) dendrimer complexes," International Journal of Pharmaceutics, 345:142-153 (2007).
Extended European Search Report and Opinion dated Sep. 5, 2016 for European Patent Application No. 14778339.3, 10 pages.
Fransson et al., "Local Tolerance of Subcutaneous Injections," J. Pharm. Pharmacol., 48:1012-1015(1996).
Ghanekar et al., "Stability of Furosemide in Aqueous Systems," Journal of Pharmaceutical Sciences, 67(6):808-811 (1978).
Granero et al., "Biowaiver Monographs for Immediate Release Solid Oral Dosage Forms: Furosemide," Journal of Pharmaceutical Sciences, 99(6):2544-2556 (2010).
Intellectual Property Office of Singapore Search Report for Application No. 11201508251R, dated Oct. 12, 2016 (2 pages).
Intellectual Property Office of Singapore Written Opinion for Application No. 11201508251R, dated Oct. 21, 2016 (5 pages).
International Search Report and Written Opinion dated May 19, 2020, for International Application No. PCT/US2020/015799, 10 pages.
International Search Report and Written Opinion dated Sep. 12, 2014, for International Application No. PCT/US2014/032800, 9 pages.
Laursen et al., "Pain Perception after Subcutaneous Injections of Media Containing Different Buffers," Basic & Clinical Pharmacology & Toxicology, 98:218-221 (2006).
Ogbru, furosemide—Preparations, https://www.medicinenet.com, Mar. 7, 2010, printed from https://web.archive.org/web/20100307214458/http://www.medicinenet.com/furosemide/article.htm, 3 pages.
Ponto et al., Furosemide (Frusemide) A Pharmacokinetic/Pharmacodynamic Review (Part II), Clin. Pharmacokinet., 18:460-471 (1990).
Sigma-Aldrich, Buffer Reference Center—Useful pH Ranges of Selected Biological Buffers, Jan. 19, 2009, printed from https://web.archive.org/web/20090119001141/https://www.sigmaaldrich.com/life-science/core-bioreagents/biological-buffers/learning-center/buffer-reference-center.html, 4 pages (Year: 2009).
Strickley, "Solubilizing Excipients in Oral and Injectable Formulations," Pharmaceutical Research, 21(2):201-230 (2004).
The Pharmaceutics and Compounding Laboratory, Guidelines, Equipment, and Supplies for Sterile Compounding—Physiological pH, University of North Carolina at Chapel Hill, Dec. 3, 2011, printed from https://web.archive.org/web/20111203230637/http:l/pharmlabs.unc.edu:80/labs/parenterals/equip.htm, 2 pages.
Verma et al., Diuretic effects of subcutaneous furosemide in human volunteers: a randomized pilot study, Ann Pharmacother, Apr. 2004;38(4):544-9, printed from https://pubmed.ncbi.nlm.nih.gov/14982985/, 2 pages, Abstract only.
Ward et al., "Discomfort from an Alkaline Formulation Delivered Subcutaneously in Humans: Albumin at pH 7 versus pH 10," Clin Drug Investig, 32(7):433-438 (2012).
www.infusionnurse.org, Is there a difference? Osmolarity vs. Osmolality . . . , May 14, 2010, printed from https://infusionnurse.org/2010/05/14/osmolarity-vs-osmolality/, 3 pages.
www.pharmacorama.com, Routes of drug administration—Parenteral route, Aug. 19, 2006, printed from http://www.pharmacorama.com/en/Sections/Pharmacokinetics-5.php, 5 pages.

CONCENTRATED LIQUID PHARMACEUTICAL FORMULATIONS OF FUROSEMIDE

CROSS-REFERENCE TO RELATED APPLICATION

This application is a continuation of U.S. patent application Ser. No. 17/675,043, filed on Feb. 18, 2022, which application is a continuation of U.S. patent application Ser. No. 17/426,765, filed on Jul. 29, 2021, which application is a U.S. national stage patent application of International Application No. PCT/US2020/015799, filed on Jan. 30, 2020, which claims the benefit of, and priority to, U.S. Patent Application No. 62/799,215, filed on Jan. 31, 2019, the content of each of which is hereby incorporated by reference in its entirety.

BACKGROUND

Furosemide, an exemplary loop diuretic, can be used in the treatment of hypertension, edema and related conditions, including decompensated heart failure. Furosemide is commonly used in the treatment and/or management of edema associated with cardiac, renal, and hepatic insufficiency or failure, for example, congestive heart failure. H. Bundgaard, T. Norgaard, N. M. Nielsen, "*Photodegradation and hydrolysis of furosemide and furosemide esters in aqueous solutions,*" International Journal of Pharmaceutics 42, 217 (1988).

Oral bioavailability, and therefore oral efficacy, of furosemide is limited. Furosemide is commonly administered both parenterally and orally, although highly variable oral absorption is observed due to the combined effects of limited solubility and decreased stability at acidic pH. B. Devarakonda, D. P. Otto, A. Judefeind, R. A. Hill, M. M. de Villiers, "*Effect of pH on the solubility and release of furosemide from polyamidoamine (PAMAM)dendrimer complexes,*" International Journal of Pharmaceutics 345, 142 (Dec. 10, 2007). Accordingly, furosemide typically is administered intravenously or intramuscularly for most patients with decompensated heart failure or other forms of more advanced edema.

Intravenous administration of a pharmaceutical drug, such as furosemide, requires a trained healthcare professional for placement of the catheter and administration of the drug solution. In contrast, subcutaneous administration of a pharmaceutical drug can be accomplished with the aid of auto-injection devices and/or minipumps or subcutaneous injections or infusions, which can permit administration to be performed by the patient or caregiver, for example, at home. Subcutaneous administration of furosemide by the patient or caregiver also can allow for more optimal therapeutic administration and total dose to provide a more appropriate pharmacokinetic and pharmacodynamic profile and patient outcome.

For subcutaneous administration, discomfort and pain during administration should be minimized so as to avoid poor patient compliance with the treatment regimen. Factors that can contribute to pain and discomfort perceived by a patient upon, during, or after subcutaneous administration include the injection volume, the pH of the formulation, and the osmoticity or tonicity of the formulation. Moreover, such a formulation should be stable in solution so that it readily is available for use and/or can be pre-loaded into a variety of dispensing devices.

Therefore, a need exists for improved pharmaceutical formulations containing furosemide that contain a sufficient concentration of furosemide, and are at an appropriate pH and osmolality, for example, to permit subcutaneous administration of furosemide.

SUMMARY

In one aspect, the invention provides a liquid pharmaceutical formulation of furosemide or a pharmaceutically acceptable salt thereof.

In various embodiments of the invention, the liquid pharmaceutical formulation comprises:
  (i) furosemide, or a pharmaceutically acceptable salt thereof;
  (ii) one or more pharmaceutically acceptable excipients; and
  (iii) a pharmaceutically acceptable buffer,
wherein the concentration of furosemide in the liquid pharmaceutical formulation is from about 40 mg/mL to about 250 mg/mL. In certain embodiments, the pH of the liquid pharmaceutical formulation is from about 6.5 to about 8.5.

In certain embodiments of the invention, the liquid pharmaceutical formulation comprises:
  (i) furosemide, or a pharmaceutically acceptable salt thereof;
  (ii) from about 0.1% (w/w) to about 30% (w/w) of one or more pharmaceutically acceptable excipients selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof; and
  (iii) from about 25 mM to about 500 mM of a pharmaceutically acceptable buffer selected from the group consisting of histidine, a citrate salt, sodium phosphate, potassium phosphate, tromethamine or a pharmaceutically acceptable salt thereof, and any combination thereof, wherein the concentration of furosemide in the liquid pharmaceutical formulation is from about 40 mg/mL to about 250 mg/mL and the pH of the liquid pharmaceutical formulation is from about 6.5 to about 8.5.

In certain embodiments of the invention, the liquid pharmaceutical formulation comprises:
  (i) furosemide, or a pharmaceutically acceptable salt thereof;
  (ii) benzyl alcohol; and
  (iii) a pharmaceutically acceptable buffer,
wherein the concentration of furosemide in the liquid pharmaceutical formulation is from about 40 mg/mL to about 250 mg/mL.

In certain embodiments of the invention, the liquid pharmaceutical formulation comprises:
  (i) furosemide, or a pharmaceutically acceptable salt thereof;
  (ii) N-methyl-pyrrolidone (NMP); and
  (iii) a pharmaceutically acceptable buffer,
wherein the concentration of furosemide in the liquid pharmaceutical formulation is from about 40 mg/mL to about 250 mg/mL.

In certain embodiments of the invention, the liquid pharmaceutical formulation comprises:
  (i) furosemide, or a pharmaceutically acceptable salt thereof;
  (ii) benzyl alcohol;

(iii) N-methyl-pyrrolidone (NMP); and
(iv) a pharmaceutically acceptable buffer,
wherein the concentration of furosemide in the liquid pharmaceutical formulation is from about 40 mg/mL to about 250 mg/mL.

In certain embodiments of the invention, the liquid pharmaceutical formulation comprises:
(i) furosemide, or a pharmaceutically acceptable salt thereof;
(ii) from about 0.1% (w/w) to about 10% (w/w) benzyl alcohol; and
(iii) from about 25 mM to about 250 mM tromethamine or a pharmaceutically acceptable salt thereof,
wherein the concentration of furosemide in the liquid pharmaceutical formulation is from about 40 mg/mL to about 250 mg/mL.

In certain embodiments of the invention, the liquid pharmaceutical formulation comprises:
(i) furosemide, or a pharmaceutically acceptable salt thereof;
(ii) from about 0.1% (w/w) to about 10% (w/w) N-methyl-pyrrolidone;
(iii) from about 0.1% (w/w) to about 10% (w/w) benzyl alcohol; and
(iv) from about 25 mM to about 250 mM tromethamine or a pharmaceutically acceptable salt thereof,
wherein the concentration of furosemide in the liquid pharmaceutical formulation is from about 40 mg/mL to about 250 mg/mL.

In another aspect, the invention provides a unit liquid pharmaceutical formulation of furosemide or a pharmaceutically acceptable salt thereof.

In certain embodiments of the invention, the unit liquid pharmaceutical formulation comprises:
(i) from about 10 mg to about 200 mg furosemide, or a pharmaceutically acceptable salt thereof;
(ii) from about 0.1% (w/w) to about 30% (w/w) of one or more pharmaceutically acceptable excipients selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof; and
(iii) from about 25 mM to about 500 mM of a pharmaceutically acceptable buffer selected from the group consisting of histidine, a citrate salt, sodium phosphate, potassium phosphate, tromethamine or a pharmaceutically acceptable salt thereof, and any combination thereof,
wherein the concentration of furosemide in the liquid pharmaceutical formulation is from about 40 mg/mL to about 250 mg/mL and wherein the pH of the liquid pharmaceutical formulation is from about 6.5 to about 8.5.

In certain embodiments of the invention, the unit liquid pharmaceutical formulation comprises:
(i) from about 10 mg to about 200 mg furosemide, or a pharmaceutically acceptable salt thereof;
(ii) from about 0.1% (w/w) to about 10% (w/w) benzyl alcohol; and
(iii) from about 25 mM to about 250 mM tromethamine or a pharmaceutically acceptable salt thereof,
wherein the concentration of furosemide in the unit liquid pharmaceutical formulation is from about 40 mg/mL to about 200 mg/mL.

In certain embodiments of the invention, the unit liquid pharmaceutical formulation comprises:
(i) from about 10 mg to about 200 mg furosemide, or a pharmaceutically acceptable salt thereof;
(ii) from about 0.1% (w/w) to about 10% (w/w) N-methyl-pyrrolidone;
(iii) from about 0.1% (w/w) to about 10% (w/w) benzyl alcohol; and
(iv) from about 25 mM to about 250 mM tromethamine or a pharmaceutically acceptable salt thereof,
wherein the concentration of furosemide in the unit liquid pharmaceutical formulation is from about 40 mg/mL to about 200 mg/mL.

In certain embodiments, the liquid pharmaceutical formulation or the unit liquid pharmaceutical formulation comprises one or more of water; a pH adjuster; and an osmolarity adjuster.

Another aspect of the invention provides a method of treating congestion, edema, fluid overload, or hypertension in a patient in need thereof, the method comprising administering to the patient a liquid pharmaceutical formulation or a unit liquid pharmaceutical formulation described herein.

Another aspect of the invention provides a kit for the treatment of congestion, edema, fluid overload, or hypertension comprising a liquid pharmaceutical formulation or a unit liquid pharmaceutical formulation described herein.

DETAILED DESCRIPTION

The invention provides liquid pharmaceutical formulations and unit liquid pharmaceutical formulations containing furosemide, medical kits containing the same, and methods of using the liquid pharmaceutical formulations and unit liquid pharmaceutical formulations to treat medical disorders e.g., congestion, edema, fluid overload, or hypertension in a patient in need thereof. In particular, the invention can provide pharmaceutical formulations including an increased concentration of furosemide, or a pharmaceutically acceptable salt thereof, using one or more pharmaceutically acceptable excipients along with a pharmaceutically acceptable buffer, which can maintain an appropriate pH for administration to a patient.

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

The terms "a" and "an" as used herein mean "one or more" and include the plural unless the context is inappropriate.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, values are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As used herein, a "compound" (including a specifically named compound, e.g., furosemide) refers to the compound itself and its pharmaceutically acceptable salts unless otherwise understood from the context of the description or expressly limited to one particular form of the compound, e.g., the compound itself, or a pharmaceutically acceptable salt thereof.

As used herein, "furosemide" refers to a compound having the formula:

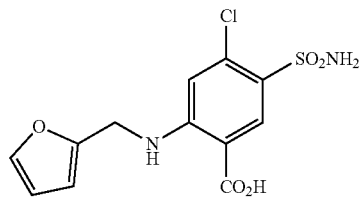 [SMILES: NS(=O)(=O)c1cc(C(=O)O)c(NCc2ccco2)cc1Cl]

and pharmaceutically acceptable salts thereof. Such salts may include, but are not limited to, furosemide sodium salt and furosemide quaternary ammonium salt. Furosemide may be referred to by other names, for example, frusemide, 5-(aminosulphonyl)-4-chloro-2[(2-furanyl-methyl)amino] benzoic acid, or its IUPAC name, 4-chloro-2-(furan-2-ylmethylamino)-5-sulfamoyl-benzoic acid, or its common trade name, Lasix®.

As used herein, the terms "subject" and "patient" refer to organisms to be treated by the methods and/or compositions described herein. Such organisms are preferably mammals (e.g., murines, simians, equines, bovines, porcines, canines, felines, and the like), and more preferably humans.

As used herein, a "buffer" refers to an aqueous solution that is resistant to changes in pH. A buffer may include a "buffering agent" such as a weak acid and its salt, or a weak base and its salt, which assist in maintaining the stability of the pH. Examples of buffers used in pharmaceutical formulations include bicarbonate buffers, carbonate buffers, citrate buffers, histidine buffers, phosphate buffers, tartrate buffers, tris(hydroxymethyl)aminomethane (or 2-amino-2-hydroxymethyl-propane-1,3-diol [(HOCH$_2$)$_3$CNH$_2$]) buffers, and combinations thereof. Certain of these buffers are suitable for pharmaceutical formulations administered subcutaneously.

Tris(hydroxymethyl)aminomethane or a tris(hydroxymethyl)aminomethane buffer can be referred to as "TRIS," "Tris," "Tris buffer," "Trisamine," "THAM," "tromethamine," and other names. In addition, many buffers and/or buffer systems can include Tris, or a pharmaceutically acceptable salt thereof, and can be used in the present teachings. For example, Tris-buffered saline ("TBS"), Tris-hydrochloride buffer ("Tris-HCl"), Tris base (pH 10.6), Tris/borate/ethylene diamine tetra-acetate ("EDTA") buffer ("TBE"), and Tris/acetate/EDTA buffer ("TAE"). Tris base often is used with Tris-HCl to prepare Tris buffers at a desired pH. In addition, the present teachings can include Tris-related compounds, for example, compounds derived from Tris or structurally-related to Tris, that can act as a buffer.

As used herein, "tonicity" refers to the ionic strength or concentration of ions in a solution such as a pharmaceutical formulation. Tonicity often is measured in molarity ("M"). As used herein, an "isotonic solution," an "isotonic formulation," an "isotonic pharmaceutical formulation," and a pharmaceutical formulation that is "isotonic" refers to a solution or formulation that has the same or similar concentration of ions as found in bodily fluids.

As used herein, "physiological pH" refers to a pH of about 7.4.

As used herein, "osmoticity" and "osmolality" refer to the osmotic pressure of a solution such as a pharmaceutical formulation. Osmoticity often is measured in osmolarity ("Osm/L" or "OsM") or osmolality ("Osm/kg"), which can be used interchangeably herein. When measuring freezing point depression, the observed value is the osmolality of the solution. In contrast to tonicity, osmoticity accounts for un-ionized solutes in a solution such that when present, the osmolarity or osmolality of the solution will be higher than its tonicity. The osmolarity of a liquid pharmaceutical formulation described herein can be measured, for example, using a vapor pressure method.

As used herein, an "isosmotic solution," an "isosmotic formulation," an "isosmotic pharmaceutical formulation," and a pharmaceutical formulation that is "isosmotic" refers to a solution or a formulation that has the same or similar concentration of solutes as found in bodily fluids. In certain embodiments, a liquid pharmaceutical formulation that is "isosmotic" can have an osmolarity in the range of about 275 mOsM to about 350 mOsM or when the osmolality of the formulation is in the range of about 275 mOsm/kg to about 350 mOsm/kg.

As used herein, "osmolarity adjustor" and "osmotic agent" refer to a pharmaceutically acceptable compound that may be added to a liquid pharmaceutical formulation described herein in order to modulate the osmolarity of the liquid pharmaceutical formulation.

As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. In certain embodiments, supplementary active ingredients can also be incorporated into the pharmaceutical compositions.

As used herein, "pharmaceutically acceptable excipient" refers to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients and carriers, see Martin, Remington's Pharmaceutical Sciences, 15th Ed., Mack Publ. Co., Easton, Pa. (1975).

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Nat, $NH_4^+$, and $NW_4^+$ (wherein W is a $C_{1-4}$ alkyl group), and the like.

As used herein, the term "effective amount" refers to the amount of a composition (e.g., a liquid pharmaceutical formulation of the present invention) sufficient to effect beneficial or desired results. An effective amount can be administered in one or more administrations, applications or dosages and is not intended to be limited to a particular formulation or administration route.

As used herein, the terms "treat," "treating," and "treatment" include any effect, e.g., lessening, reducing, modulating, ameliorating or eliminating, that results in the improvement of the condition, disease, disorder, and the like, or ameliorating a symptom thereof.

The phrase "therapeutically-effective amount" as used herein means that amount of a composition (e.g., a liquid pharmaceutical formulation of the present invention) which is effective for producing some desired therapeutic effect in a subject.

As used herein, the term "congestion" (in heart failure) is the presence of signs and symptoms of extracellular fluid accumulation that results in increased cardiac filling pressures leading to reduced cardiac output. This reduced cardiac output is further exacerbated by neurohormonal activation leading to increased renal sodium and water avidity resulting in an increased plasma volume.

As used herein, "fluid overload," "volume overload" and "hypervolemia", may describe a medical condition where there is too much fluid in the blood. Excess fluid, primarily salt and water, may build up throughout the body resulting in weight gain.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

Liquid Pharmaceutical Formulations of Furosemide

As described herein, in one aspect, the invention provides liquid pharmaceutical formulations of furosemide or a pharmaceutically acceptable salt thereof.

In various embodiments, a liquid pharmaceutical formulation generally comprises:
  (i) furosemide, or a pharmaceutically acceptable salt thereof;
  (ii) one or more pharmaceutically acceptable excipients; and
  (iii) a pharmaceutically acceptable buffer,
wherein the concentration of furosemide in the liquid pharmaceutical formulation is from about 40 mg/mL to about 250 mg/mL.

In various embodiments, the one or more pharmaceutically acceptable excipients is selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof. In certain embodiments, the PEG has a weight average molecular weight of from about 3000 g/mol to about 3700 g/mol. In certain embodiments, the polysorbate is polysorbate 80. In certain embodiments, the PVP has a weight average molecular weight of about 4000 g/mol to about 6000 g/mol. In certain embodiments, the cyclodextrin is β-cyclodextrin.

In certain embodiments, the amount of the one or more pharmaceutically acceptable excipients in the liquid pharmaceutical formulations described herein can be from about 0.1% (w/w) to about 30% (w/w), from about 0.5% (w/w) to about 30% (w/w), from about 1% (w/w) to about 30% (w/w), from about 1.5% (w/w) to about 30% (w/w), (w/w), from about 2% (w/w) to about 30% (w/w), from about 2.5% (w/w) to about 30% (w/w), from about 3% (w/w) to about 30% (w/w), from about 3.5% (w/w) to about 30% (w/w), from about 4% (w/w) to about 30% (w/w), from about 4.5% (w/w) to about 30% (w/w), from about 5% (w/w) to about 30% (w/w), from about 10% (w/w) to about 30% (w/w), from about 15% (w/w) to about 30% (w/w), from about 20% (w/w) to about 30% (w/w), from about 25% (w/w) to about 30% (w/w), from about 0.1% (w/w) to about 25% (w/w), from about 0.1% (w/w) to about 20% (w/w), from about 0.1% (w/w) to about 15% (w/w), from about 0.1% (w/w) to about 10% (w/w), from about 0.1% (w/w) to about 5% (w/w), from about 0.1% (w/w) to about 4.5% (w/w), from about 0.1% (w/w) to about 4% (w/w), from about 0.1% (w/w) to about 3.5% (w/w), from about 0.1% (w/w) to about 3% (w/w), from about 0.1% (w/w) to about 2.5% (w/w), from about 0.1% (w/w) to about 2% (w/w), from about 0.1% (w/w) to about 1.5% (w/w), from about 0.1% (w/w) to about 1% (w/w), from about 0.1% (w/w) to about 0.5% (w/w), from about 0.5% (w/w) to about 25% (w/w), from about 0.5% (w/w) to about 20% (w/w), from about 0.5% (w/w) to about 15% (w/w), from about 0.5% (w/w) to about 10% (w/w), from about 0.5% (w/w) to about 5% (w/w), from about 0.5% (w/w) to about 4.5% (w/w), from about 0.5% (w/w) to about 4% (w/w), from about 0.5% (w/w) to about 3.5% (w/w), from about 0.5% (w/w) to about 3% (w/w), from about 0.5% (w/w) to about 2.5% (w/w), from about 0.5% (w/w) to about 2% (w/w), from about 0.5% (w/w) to about 1.5% (w/w), from about 0.5% (w/w) to about 1% (w/w), from about 1% (w/w) to about 25% (w/w), from about 1% (w/w) to about 20% (w/w), from about 1% (w/w) to about 15% (w/w), from about 1% (w/w) to about 10% (w/w), from about 1% (w/w) to about 5% (w/w), from about 1% (w/w) to about 4.5% (w/w), from about 1% (w/w) to about 4% (w/w), from about 1% (w/w) to about 3.5% (w/w), from about 1% (w/w) to about 2.5% (w/w), from about 1% (w/w) to about 2% (w/w), from about 1% (w/w) to about 1.5% (w/w), from about 1.5% (w/w) to about 25% (w/w), from about 1.5% (w/w) to about 20% (w/w), from about 1.5% (w/w) to about 15% (w/w), from about 1.5% (w/w) to about 10% (w/w), from about 1.5% (w/w) to about 5% (w/w), from about 1.5% (w/w) to about 4.5% (w/w), from about 1.5% (w/w) to about 4% (w/w), from about 1.5% (w/w) to about 3.5% (w/w), from about 1.5% (w/w) to about 3% (w/w), from about 1.5% (w/w) to about 2.5% (w/w), from about 1.5% (w/w) to about 2% (w/w), from about 2% (w/w) to about 25% (w/w), from about 2% (w/w) to about 20% (w/w), from about 2% (w/w) to about 15% (w/w), from about 2% (w/w) to about 10% (w/w), from about 2% (w/w) to about 5% (w/w), from about 2% (w/w) to about 4.5% (w/w), from about 2% (w/w) to about 4% (w/w), from about 2% (w/w) to about 3.5% (w/w), from about 2% (w/w) to about 3% (w/w), from about 2% (w/w) to about 2.5% (w/w), from about 2.5% (w/w) to about 25% (w/w), from about 2.5% (w/w) to about 20% (w/w), from about 2.5% (w/w) to about 15% (w/w), from about 2.5% (w/w) to about 10% (w/w), from about 2.5% (w/w) to about 5% (w/w), from about 2.5% (w/w) to about 4.5% (w/w), from about 2.5% (w/w) to about 4% (w/w), from about 2.5% (w/w) to about 3.5% (w/w), from about 2.5% (w/w) to about 3% (w/w), from about 3% (w/w) to about 25% (w/w), from about 3% (w/w) to about 20% (w/w), from about 3% (w/w) to about 15% (w/w), from about 3% (w/w) to about 10% (w/w), from about 3% (w/w) to about 5% (w/w), from about 3% (w/w) to about 4.5% (w/w), from about 3% (w/w) to about 4% (w/w), from about 3% (w/w) to about 3.5% (w/w), from about 3.5% (w/w) to about 25% (w/w), from about 3.5% (w/w) to about 20% (w/w), from about 3.5% (w/w) to about 15% (w/w), from about 3.5% (w/w) to about 10% (w/w), from about 3.5% (w/w) to about 5% (w/w), from about 3.5% (w/w) to about 4.5% (w/w), from about 3.5% (w/w) to about 4% (w/w), from about 4% (w/w) to about 25% (w/w), from about 4% (w/w) to about 20% (w/w), from about 4% (w/w) to about 15% (w/w), from about 4% (w/w) to about 10% (w/w), from about 4% (w/w) to about 5% (w/w), from about 4% (w/w) to about 4.5% (w/w), from about 4.5% (w/w) to about 25% (w/w), from about 4.5% (w/w) to about 20% (w/w), from about 4.5% (w/w) to about 15% (w/w), from about 4.5% (w/w) to about 10% (w/w), from about 4.5% (w/w) to about 5% (w/w), from about 5% (w/w) to about 25% (w/w), from about 5% (w/w) to about 20% (w/w), from about 5% (w/w) to about 15% (w/w), from about 5% (w/w) to about 10% (w/w), from about 10% (w/w) to about 25% (w/w), from about 10% (w/w) to about 20% (w/w), from about 10% (w/w) to about 15% (w/w), from about 15% (w/w) to about 25% (w/w), from about 15% (w/w) to about 20% (w/w), or from about 20% (w/w) to about 25% (w/w). In certain embodiments, the amount of the one or more pharmaceutically acceptable excipients in the liquid pharmaceutical formulation is from about 1.5% (w/w) to about 30% (w/w). In certain embodiments, the amount of the one or more pharmaceutically acceptable excipients in the liquid pharmaceutical formulation is from about 5% (w/w) to about 15% (w/w). In certain embodiments, the amount of the one or more pharmaceutically acceptable excipients in the liquid pharmaceutical formulation is from about 0.1% (w/w) to about 10% (w/w). In certain embodiments, the amount of the one or more pharmaceutically acceptable excipients in the liquid pharmaceutical formulation is from about 0.5% (w/w) to about 5% (w/w).

In various embodiments, the amount of the one or more pharmaceutically acceptable excipients in the liquid pharmaceutical formulations described herein can about 0.1% (w/w), about 0.25% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), or about 30% (w/w).

In certain embodiments, the one or more pharmaceutically acceptable excipients comprises benzyl alcohol. In certain embodiments, the one or more pharmaceutically acceptable excipients comprises NMP. In certain embodiments, the one or more pharmaceutically acceptable excipients comprises NMP and benzyl alcohol.

In various embodiments, a liquid pharmaceutical formulation comprises:
  (i) furosemide, or a pharmaceutically acceptable salt thereof;
  (ii) benzyl alcohol; and
  (iii) a pharmaceutically acceptable buffer,
wherein the concentration of furosemide in the liquid pharmaceutical formulation is from about 40 mg/mL to about 250 mg/mL.

In certain embodiments, the liquid pharmaceutical formulation further comprises N-methyl-pyrrolidone (NMP).

In various embodiments, a liquid pharmaceutical formulation comprises:
  (i) furosemide, or a pharmaceutically acceptable salt thereof;
  (ii) benzyl alcohol;
  (iii) N-methyl-pyrrolidone (NMP); and
  (iv) a pharmaceutically acceptable buffer,
wherein the concentration of furosemide in the liquid pharmaceutical formulation is from about 40 mg/mL to about 250 mg/mL.

In various embodiments, the amount of benzyl alcohol in the liquid pharmaceutical formulations described herein can be from about 0.1% (w/w) to about 10% (w/w), from about 0.5% (w/w) to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 0.1% (w/w) to about 5% (w/w), from about 0.1% (w/w) to about 4% (w/w), from about 0.1% (w/w) to about 3% (w/w), from about 0.1% (w/w) to about 2% (w/w), from about 0.1% (w/w) to about 1% (w/w), from about 0.1% (w/w) to about 0.5% (w/w), from about 0.5% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 5% (w/w), from about 2% (w/w) to about 4% (w/w), from about 2% (w/w) to about 3% (w/w), from about 3% (w/w) to about 5% (w/w), from about 3% (w/w) to about 4% (w/w), or from about 4% (w/w) to about 5% (w/w). In certain embodiments, the amount of benzyl alcohol in the liquid pharmaceutical formulation is from about 0.1% (w/w) to about 10% (w/w). In certain embodiments, the amount of benzyl alcohol in the liquid pharmaceutical formulation is from about 0.5% (w/w) to about 5% (w/w).

In various embodiments, the amount of benzyl alcohol in the liquid pharmaceutical formulations described herein can be about 0.1% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 6% (w/w), about 7% (w/w), about 8% (w/w), about 9% (w/w), or about 10% (w/w). In certain embodiments, the amount of benzyl alcohol in the liquid pharmaceutical formulation is about 4% (w/w).

In various embodiments, the amount of NMP in the liquid pharmaceutical formulations described herein can be from about 0.1% (w/w) to about 10% (w/w), from about 0.5% (w/w) to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 0.1% (w/w) to about 5% (w/w), from about 0.1% (w/w) to about 4% (w/w), from about 0.1% (w/w) to about 3% (w/w), from about 0.1% (w/w) to about 2% (w/w), from about 0.1% (w/w) to about 1% (w/w), from about 0.1% (w/w) to about 0.5% (w/w), from about 0.5% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 5% (w/w), from about 2% (w/w) to about 4% (w/w), from about 2% (w/w) to about 3% (w/w), from about 3% (w/w) to about 5% (w/w), from about 3% (w/w) to about 4% (w/w), or from about 4% (w/w) to about 5% (w/w). In certain embodiments, the amount of NMP in the liquid pharmaceutical formulation is from about 0.1% (w/w) to about 10% (w/w). In certain embodiments, the amount of NMP in the liquid pharmaceutical formulation is from about 0.1% (w/w) to about 1% (w/w).

In various embodiments, the amount of NMP in the liquid pharmaceutical formulations described herein can be about 0.1% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), or about 10% (w/w). In some embodiments, the amount of NMP in the liquid pharmaceutical formulation is about 0.5 (w/w).

In various embodiments, a liquid pharmaceutical formulation comprises:
  (i) furosemide, or a pharmaceutically acceptable salt thereof;
  (ii) N-methyl-pyrrolidone (NMP); and
  (iii) a pharmaceutically acceptable buffer, wherein the concentration of furosemide in the liquid pharmaceutical formulation is from about 40 mg/mL to about 250 mg/mL.

In various embodiments, the amount of NMP in the liquid pharmaceutical formulations described herein can be from about 1% (w/w) to about 25% (w/w), from about 2.5% (w/w) to about 25% (w/w), from about 5% (w/w) to about 25% (w/w), from about 7.5% (w/w) to about 25% (w/w), from about 10% (w/w) to about 25% (w/w), from about 12.5% (w/w) to about 25% (w/w), from about 15% (w/w) to about 25% (w/w), from about 20% (w/w) to about 25% (w/w), from about 1% (w/w) to about 20% (w/w), from about 1% (w/w) to about 15% (w/w), from about 1% (w/w) to about 12.5% (w/w), from about 1% (w/w) to about 10% (w/w), from about 1% (w/w) to about 7.5% (w/w), from about 1% (w/w) to about 5% (w/w), from about 1% (w/w) to about 2.5% (w/w), from about 2.5% (w/w) to about 20% (w/w), from about 2.5% (w/w) to about 15% (w/w), from about 2.5% (w/w) to about 12.5% (w/w), from about 2.5% (w/w) to about 10% (w/w), from about 2.5% (w/w) to about 7.5% (w/w), from about 2.5% (w/w) to about 5% (w/w), from about 5% (w/w) to about 20% (w/w), from about 5% (w/w) to about 15% (w/w), from about 5% (w/w) to about 12.5% (w/w), from about 5% (w/w) to about 10% (w/w), from about 5% (w/w) to about 7.5% (w/w), from about 7.5% (w/w) to about 20% (w/w), from about 7.5% (w/w) to about 15% (w/w), from about 7.5% (w/w) to about 12.5% (w/w), from about 7.5% (w/w) to about 10% (w/w), from about 10% (w/w) to about 20% (w/w), from about 10% (w/w) to about 15% (w/w), from about 10% (w/w) to about 12.5% (w/w), from about 12.5% (w/w) to about 20% (w/w), from about 12.5% (w/w) to about 15% (w/w), from about 12.5% (w/w) to about 20% (w/w), from about 12.5% (w/w) to about 15% (w/w), or from about 15% (w/w) to about 20% (w/w). In certain embodiments, the amount of NMP in the liquid pharmaceutical formulation is from about 1% (w/w) to about 25% (w/w). In certain embodiments, the amount of NMP in the liquid pharmaceutical formulation is from about 5% (w/w) to about 10% (w/w).

In various embodiments, the amount of NMP in the liquid pharmaceutical formulations described herein can be about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 12.5% (w/w), about 15% (w/w), about 20% (w/w), or about 25% (w/w).

In certain embodiments, the liquid pharmaceutical formulation further comprises benzyl alcohol.

In various embodiments, the amount of benzyl alcohol in the liquid pharmaceutical formulations described herein can be from about 0.5% (w/w) to about 5% (w/w), from about 1% (w/w) to about 5% (w/w), from about 2% (w/w) to about 5% (w/w), from about 3% (w/w) to about 5% (w/w), from about 4% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 4% (w/w), from about 1% (w/w) to about 3% (w/w), from about 1% (w/w) to about 2% (w/w), from about 2% (w/w) to about 4% (w/w), from about 2% (w/w) to about 3% (w/w), or from about 3% (w/w) to about 4% (w/w). In certain embodiments, the amount of benzyl alcohol in the liquid pharmaceutical formulation is from about 0.5% (w/w) to about 5% (w/w). In certain embodiments, the amount of benzyl alcohol in the liquid pharmaceutical formulation is from about 1% (w/w) to about 3% (w/w).

In various embodiments, the amount of benzyl alcohol in the liquid pharmaceutical formulations described herein can be about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), or about 5% (w/w).

In various embodiments, the concentration of the pharmaceutically acceptable buffer in the liquid pharmaceutical formulations described herein can be from about 25 mM to about 500 mM, from about 30 mM to about 500 mM, from about 40 mM to about 500 mM, from about 50 mM to about 500 mM, from about 75 mM to about 500 mM, from about 100 mM to about 500 mM, from about 150 mM to about 500 mM, from about 200 mM to about 500 mM, from about 200 mM to about 500 mM, from about 250 mM to about 500 mM, from about 300 mM to about 500 mM, from about 350 mM to about 500 mM, from about 400 mM to about 500 mM, from about 450 mM to about 500 mM, from about 25 mM to about 450 mM, from about 25 mM to about 400 mM, from about 25 mM to about 350 mM, from about 25 mM to about 300 mM, from about 25 mM to about 250 mM, from about 25 mM to about 200 mM, from about 25 mM to about 150 mM, from about 25 mM to about 100 mM, from about 25 mM to about 75 mM, from about 25 mM to about 50 mM, from about 25 mM to about 40 mM, from about 25 mM to about 30 mM, from about 30 mM to about 450 mM, from about 30 mM to about 400 mM, from about 30 mM to about 350 mM, from about 30 mM to about 300 mM, from about 30 mM to about 250 mM, from about 30 mM to about 200 mM, from about 30 mM to about 150 mM, from about 30 mM to about 100 mM, from about 30 mM to about 75 mM, from about 30 mM to about 50 mM, from about 30 mM to about 40 mM, from about 40 mM to about 450 mM, from about 40 mM to about 400 mM, from about 40 mM to about 350 mM, from about 40 mM to about 300 mM, from about 40 mM to about 250 mM, from about 40 mM to about 200 mM, from about 40 mM to about 150 mM, from about 40 mM to about 100 mM, from about 40 mM to about 75 mM, from about 40 mM to about 50 mM, from about 50 mM to about 450 mM, from about 50 mM to about 400 mM, from about 50 mM to about 350 mM, from about 50 mM to about 300 mM, from about 50 mM to about 250 mM, from about 50 mM to about 200 mM, from about 50 mM to about 150 mM, from about 50 mM to about 100 mM, from about 50 mM to about 75 mM, from about 75 mM to about 450 mM, from about 75 mM to about 400 mM, from about 75 mM to about 350 mM, from about 75 mM to about 300 mM, from about 75 mM to about 250 mM, from about 75 mM to about 200 mM, from about 75 mM to about 150 mM, from about 75 mM to about 100 mM, from about 100 mM to about 450 mM, from about 100 mM to about 400 mM, from about 100 mM to about 350 mM, from about 100 mM to about 300 mM, from about 100 mM to about 250 mM, from about 100 mM to about 200 mM, from about 100 mM to about 150 mM, from about 150 mM to about 450 mM, from about 150 mM to about 400 mM, from about 150 mM to about 350 mM, from about 150 mM to about 300 mM, from about 150 mM to about 250 mM, from about 150 mM to about 200 mM, from about 200 mM to about 450 mM, from about 200 mM to about 400 mM, from about 200 mM to about 350 mM, from about 200 mM to about 300 mM, from about 200 mM to about 250 mM, from about 250 mM to about 450 mM, from about 250 mM to about 400 mM, from about 250 mM to about 350 mM, from about 250 mM to about 300 mM, from about 300 mM to about 450 mM, from about 300 mM to about 400 mM, from about 300 mM to about 350 mM, from about 350 mM to about 450 mM, from about 350 mM to about 400 mM, or from about 400 mM to about 450 mM. In certain embodiments, the concentration of the pharmaceutically acceptable buffer in the liquid pharmaceutical formulation is from about 25 mM to about 250 mM. In certain embodiments, the concentration of the pharmaceutically acceptable buffer in the liquid pharmaceutical formulation is from about 25 mM to about 100 mM.

In various embodiments, the pharmaceutically acceptable buffer comprises a buffering agent selected from the group consisting of histidine, a citrate salt, sodium phosphate, potassium phosphate, tromethamine or a pharmaceutically acceptable salt thereof, and any combination thereof.

In certain embodiments, the buffering agent is tromethamine or a pharmaceutically acceptable salt thereof. In some embodiments, the pharmaceutically acceptable salt of tromethamine is tromethamine hydrochloride.

In various embodiments, a liquid pharmaceutical formulation comprises:
  (i) furosemide, or a pharmaceutically acceptable salt thereof;
  (ii) from about 0.1% (w/w) to about 10% (w/w) benzyl alcohol;
  (iii) from about 25 mM to about 250 mM tromethamine or a pharmaceutically acceptable salt thereof,
wherein the concentration of furosemide in the liquid pharmaceutical formulation is from about 40 mg/mL to about 250 mg/mL.

In various embodiments, a liquid pharmaceutical formulation comprises:
  (i) furosemide, or a pharmaceutically acceptable salt thereof;
  (ii) from about 0.1% (w/w) to about 10% (w/w) benzyl alcohol;
  (iii) from about 0.1% (w/w) to about 10% (w/w) N-methyl-pyrrolidone (NMP);
  (iv) from about 25 mM to about 250 mM tromethamine or a pharmaceutically acceptable salt thereof,
wherein the concentration of furosemide in the liquid pharmaceutical formulation is from about 40 mg/mL to about 250 mg/mL.

In various embodiments, a liquid pharmaceutical formulation comprises:
  (i) furosemide, or a pharmaceutically acceptable salt thereof;
  (ii) from about 1% (w/w) to about 25% (w/w) N-methyl-pyrrolidone (NMP);
  (iii) from about 0.5% (w/w) to about 5% (w/w) benzyl alcohol; and
  (iv) from about 25 mM to about 250 mM tromethamine or a pharmaceutically acceptable salt thereof,
wherein the concentration of furosemide in the liquid pharmaceutical formulation is from about 40 mg/mL to about 250 mg/mL.

In various embodiments, the concentration of tromethamine or a pharmaceutically acceptable salt thereof in the liquid pharmaceutical formulations described herein can be from about 25 mM to about 250 mM, from about 50 mM to about 250 mM, from about 75 mM to about 250 mM, from about 100 mM to about 250 mM, from about 125 mM to about 250 mM, from about 150 mM to about 250 mM, from about 175 mM to about 250 mM, from about 200 mM to about 250 mM, from about 225 mM to about 250 mM, from about 25 mM to about 225 mM, from about 25 mM to about 200 mM, from about 25 mM to about 175 mM, from about 25 mM to about 150 mM, from about 25 mM to about 125 mM, from about 25 mM to about 100 mM, from about 25 mM to about 75 mM, from about 25 mM to about 50 mM, from about 50 mM to about 225 mM, from about 50 mM to about 200 mM, from about 50 mM to about 175 mM, from about 50 mM to about 150 mM, from about 50 mM to about 125 mM, from about 50 mM to about 100 mM, from about 50 mM to about 75 mM, from about 75 mM to about 225 mM, from about 75 mM to about 200 mM, from about 75 mM to about 175 mM, from about 75 mM to about 150 mM, from about 75 mM to about 125 mM, from about 75 mM to about 100 mM, from about 100 mM to about 225 mM, from about 100 mM to about 200 mM, from about 100 mM to about 175 mM, from about 100 mM to about 150 mM, from about 100 mM to about 125 mM, from about 125 mM to about 225 mM, from about 125 mM to about 200 mM, from about 125 mM to about 175 mM, from about 125 mM to about 150 mM, from about 150 mM to about 225 mM, from about 150 mM to about 200 mM, from about 150 mM to about 175 mM, from about 150 mM to about 250 mM, from about 175 mM to about 225 mM, from about 175 mM to about 200 mM, or from about 200 mM to about 225 mM. In certain embodiments, the concentration of tromethamine or a pharmaceutically acceptable salt thereof in the liquid pharmaceutical formulation is from about 25 mM to about 250 mM. In certain embodiments, the concentration of tromethamine or a pharmaceutically acceptable salt thereof in the liquid pharmaceutical formulation is from about 25 mM to about 100 mM.

In various embodiments, the concentration of tromethamine or a pharmaceutically acceptable salt thereof in the liquid pharmaceutical formulations described herein can be about 25 mM, about 50 mM, about 75 mM, about 100 mM, about 125 mM, about 150 mM, about 175 mM, about 200 mM, about 225 mM, or about 250 mM. In certain embodiments, the concentration of tromethamine or a pharmaceutically acceptable salt thereof in the liquid pharmaceutical formulation is about 50 mM.

In various embodiments, the concentration of furosemide in the liquid pharmaceutical formulations described herein can be from about 50 mg/mL to about 250 mg/mL, from about 60 mg/mL to about 250 mg/mL, from about 70 mg/mL to about 250 mg/mL, from about 80 mg/mL to about 250 mg/mL, from about 90 mg/mL to about 250 mg/mL, from about 100 mg/mL to about 250 mg/mL, from about 120 mg/mL to about 250 mg/mL, from about 140 mg/mL to about 250 mg/mL, from about 160 mg/mL to about 250 mg/mL, from about 180 mg/mL to about 250 mg/mL, from about 200 mg/mL to about 250 mg/mL, from about 50 mg/mL to about 200 mg/mL, from about 50 mg/mL to about 180 mg/mL, from about 50 mg/mL to about 160 mg/mL, from about 50 mg/mL to about 140 mg/mL, from about 50 mg/mL to about 120 mg/mL, from about 50 mg/mL to about 100 mg/mL, from about 50 mg/mL to about 90 mg/mL, from about 50 mg/mL to about 80 mg/mL, from about 50 mg/mL to about 70 mg/mL, from about 50 mg/mL to about 60 mg/mL, from about 60 mg/mL to about 200 mg/mL, from about 60 mg/mL to about 180 mg/mL, from about 60 mg/mL to about 160 mg/mL, from about 60 mg/mL to about 140 mg/mL, from about 60 mg/mL to about 120 mg/mL, from about 60 mg/mL to about 100 mg/mL, from about 60 mg/mL to about 90 mg/mL, from about 60 mg/mL to about 80 mg/mL, from about 60 mg/mL to about 70 mg/mL, from about 70 mg/mL to about 200 mg/mL, from about 70 mg/mL to about 180 mg/mL, from about 70 mg/mL to about 160 mg/mL, from about 70 mg/mL to about 140 mg/mL, from about 70 mg/mL to about 120 mg/mL, from about 70 mg/mL to about 100 mg/mL, from about 70 mg/mL to about 90 mg/mL, from about 70 mg/mL to about 80 mg/mL, from about 80 mg/mL to about 200 mg/mL, from about 80 mg/mL to about 180 mg/mL, from about 80 mg/mL to about 160 mg/mL, from about 80 mg/mL to about 140 mg/mL, from about 80 mg/mL to about 120 mg/mL, from about 80 mg/mL to about 100 mg/mL, from about 80 mg/mL to about 90 mg/mL, from about 90 mg/mL to about 200 mg/mL, from about 90 mg/mL to about 180 mg/mL, from about 90 mg/mL to about 160 mg/mL, from about 90 mg/mL to about 140 mg/mL, from about 90 mg/mL to about 120 mg/mL, from about 90 mg/mL to about 100 mg/mL, from about 100 mg/mL to about 200 mg/mL, from about 100 mg/mL to about 180 mg/mL, from about 100 mg/mL to about 160 mg/mL, from about 100 mg/mL to about 140 mg/mL, from about 100 mg/mL to about 120 mg/mL, from about 120 mg/mL to about 200 mg/mL, from about 120 mg/mL to about 180 mg/mL, from about 120 mg/mL to about 160 mg/mL, from about 120 mg/mL to about 140 mg/mL, from about 140 mg/mL to about 200 mg/mL, from about 140 mg/mL to about 180 mg/mL, from about 140 mg/mL to about 160 mg/mL, from about 160 mg/mL to about 200 mg/mL, from about 160 mg/mL to about 180 mg/mL, or from about 180 mg/mL to about 200 mg/mL. In certain embodiments, the concentration of furosemide in the liquid pharmaceutical formulation is from about 50 mg/mL to about 250 mg/mL, from about 60 mg/mL to about 250 mg/mL, from about 70 mg/mL to about 250 mg/mL, or from about 80 mg/mL to about 250 mg/mL. In certain embodiments, the concentration of furosemide in the liquid pharmaceutical formulation is from about 80 mg/mL to about 250 mg/mL.

In various embodiments, the concentration of furosemide in the liquid pharmaceutical formulations described herein can be greater than about 40 mg/mL, greater than about 50 mg/mL, greater than about 60 mg/mL, greater than about 70 mg/mL, greater than about 80 mg/mL, greater than about 90 mg/mL, greater than about 100 mg/mL, greater than about 120 mg/mL, greater than about 140 mg/mL, greater than about 160 mg/mL, greater than about 180 mg/mL, greater than about 200 mg/mL, greater than about 220 mg/mL, or greater than about 250 mg/mL. In certain embodiments, the concentration of furosemide in the liquid pharmaceutical formulation is greater than about 40 mg/mL. In certain embodiments, the concentration of furosemide in the liquid pharmaceutical formulation is greater than about 50 mg/mL. In certain embodiments, the concentration of furosemide in the liquid pharmaceutical formulation is greater than about 60 mg/mL. In certain embodiments, the concentration of furosemide in the liquid pharmaceutical formulation is greater than about 70 mg/mL. In certain embodiments, the concentration of furosemide in the liquid pharmaceutical formulation is greater than about 80 mg/mL.

In various embodiments, the concentration of furosemide in the liquid pharmaceutical formulations described herein can be about 40 mg/mL, about 50 mg/mL, about 60 mg/mL, about 70 mg/mL, about 80 mg/mL, about 90 mg/mL, about 100 mg/mL, about 120 mg/mL, about 140 mg/mL, about 160 mg/mL, about 180 mg/mL, about 200 mg/mL, about 220 mg/mL, or about 250 mg/mL. In certain embodiments, the concentration of furosemide in the liquid pharmaceutical formulation is about 100 mg/mL.

In various embodiments, a liquid pharmaceutical formulation comprises:
(i) 100 mg/mL of furosemide, or a pharmaceutically acceptable salt thereof;
(ii) about 4% (w/w) benzyl alcohol; and
(iii) about 50 mM tromethamine or a pharmaceutically acceptable salt thereof.

In various embodiments, a liquid pharmaceutical formulation comprises:
(i) 100 mg/mL of furosemide, or a pharmaceutically acceptable salt thereof;
(ii) about 4% (w/w) benzyl alcohol;
(iii) about 0.5 (w/w) N-methyl-pyrrolidone; and
(iv) about 50 mM tromethamine or a pharmaceutically acceptable salt thereof.

In various embodiments, a liquid pharmaceutical formulation comprises:
(i) furosemide, or a pharmaceutically acceptable salt thereof;
(ii) from about 0.1% (w/w) to about 30% (w/w) of one or more pharmaceutically acceptable excipients selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof; and
(iii) from about 25 mM to about 500 mM of a pharmaceutically acceptable buffer selected from the group consisting of histidine, a citrate salt, sodium phosphate, potassium phosphate, tromethamine or a pharmaceutically acceptable salt thereof, and any combination thereof,
wherein the concentration of furosemide in the liquid pharmaceutical formulation is from about 40 mg/mL to about 250 mg/mL and the pH of the liquid pharmaceutical formulation is from about 6.5 to about 8.5.

In various embodiments, the pH of the liquid pharmaceutical formulations described herein can be from about 5.5 to about 8.5, from about 6 to about 8.5, from about 6.5 to about 8.5, from about 7 to about 8.5, from about 7.5 to about 8.5, from about 8 to about 8.5, from about 5.5 to about 8, from about 5.5 to about 7.5, from about 5.5 to about 7, from about 5.5 to about 6.5, from about 5.5 to about 6, from about 6 to about 8, from about 6 to about 7.5, from about 6 to about 7, from about 6 to about 6.5, from about 6.5 to about 8, from about 6.5 to about 7.5, from about 6.5 to about 7, from about 7 to about 8, from about 7 to about 7.5, or from about 7.5 to about 8. In certain embodiments, the pH of the liquid pharmaceutical formulation is from about 6.5 to about 8.5. In certain embodiments, the pH of the liquid pharmaceutical formulation is from about 7 to about 8. In certain embodiments, the pH of the liquid pharmaceutical formulation is from about 5.5 to about 6.5.

In various embodiments, the pH of the liquid pharmaceutical formulations described herein can be about 5.5, about 6, about 6.5, about 7, about 7.5, about 8, or about 8.5. In certain embodiments, the pH of the liquid pharmaceutical formulation is about 7.4.

In various embodiments, the pH of the liquid pharmaceutical formulations described herein can be 5.5±0.1, 6±0.1, 6.5±0.1, 7±0.1, 7.5±0.1, 8±0.1, or 8.5±0.1. In certain embodiments, the pH of the liquid pharmaceutical formulation is about 7.4±0.1.

In various embodiments, a liquid pharmaceutical formulation comprises:
(i) furosemide, or a pharmaceutically acceptable salt thereof;
(ii) benzyl alcohol; and
(iii) a pharmaceutically acceptable buffer,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, a liquid pharmaceutical formulation comprises:
(i) furosemide, or a pharmaceutically acceptable salt thereof;
(ii) N-methyl-pyrrolidone (NMP); and
(iii) a pharmaceutically acceptable buffer,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, a liquid pharmaceutical formulation comprises:
(i) furosemide, or a pharmaceutically acceptable salt thereof;
(ii) benzyl alcohol;
(iii) N-methyl-pyrrolidone (NMP); and
(iv) a pharmaceutically acceptable buffer,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, a liquid pharmaceutical formulation comprises:
(i) furosemide, or a pharmaceutically acceptable salt thereof;
(ii) from about 0.1% (w/w) to about 10% (w/w) benzyl alcohol; and
(iii) from about 25 mM to about 250 mM tromethamine or a pharmaceutically acceptable salt thereof,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, a liquid pharmaceutical formulation comprises:
(i) furosemide, or a pharmaceutically acceptable salt thereof;
(ii) from about 0.1% (w/w) to about 10% (w/w) N-methyl-pyrrolidone;
(iii) from about 0.1% (w/w) to about 10% (w/w) benzyl alcohol; and
(iv) from about 25 mM to about 250 mM tromethamine or a pharmaceutically acceptable salt thereof,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, a liquid pharmaceutical formulation comprises:
(i) furosemide, or a pharmaceutically acceptable salt thereof;
(ii) from about 1% (w/w) to about 25% (w/w) N-methyl-pyrrolidone;
(iii) from about 0.5% (w/w) to about 5% (w/w) benzyl alcohol; and
(iv) from about 25 mM to about 250 mM tromethamine or a pharmaceutically acceptable salt thereof,
wherein the concentration of furosemide in the liquid pharmaceutical formulation is from about 5 mg/mL to about 100 mg/mL and the pH of the liquid pharmaceutical formulation is about from about 5.5 to about 6.5.

In various embodiments, the concentration of furosemide in the liquid pharmaceutical formulations described herein can be from about 5 mg/mL to about 100 mg/mL, from about 10 mg/mL to about 100 mg/mL, from about 5 mg/mL to about 50 mg/mL, from about 5 mg/mL to about 40 mg/mL, from about 5 mg/mL to about 30 mg/mL, from about 5 mg/mL to about 20 mg/mL, from about 5 mg/mL to about 10 mg/mL, from about 10 mg/mL to about 50 mg/mL, from about 10 mg/mL to about 40 mg/mL, from about 10 mg/mL to about 30 mg/mL, from about 10 mg/mL to about 20 mg/mL, from about 20 mg/mL to about 100 mg/mL, from about 30 mg/mL to about 100 mg/mL, from about 40 mg/mL to about 100 mg/mL, from about 50 mg/mL to about 100 mg/mL, from about 20 mg/mL to about 50 mg/mL, from about 20 mg/mL to about 40 mg/mL, from about 20 mg/mL to about 30 mg/mL, from about 30 mg/mL to about 50 mg/mL, from about 30 mg/mL to about 40 mg/mL, or from about 40 mg/mL to about 50 mg/mL.

In certain embodiments, the concentration of furosemide in the liquid pharmaceutical formulation is from about 20 mg/mL to about 100 mg/mL. In certain embodiments, the concentration of furosemide in the liquid pharmaceutical formulation is from about 5 mg/mL to about 20 mg/mL.

In various embodiments, the concentration of furosemide in the liquid pharmaceutical formulations described herein can be greater than about 5 mg/mL, greater than about 10 mg/mL, greater than about 20 mg/mL, greater than about 30 mg/mL, greater than about 40 mg/mL, greater than about 50 mg/mL, greater than about 60 mg/mL, greater than about 70 mg/mL, greater than about 80 mg/mL, greater than about 90 mg/mL, or greater than about 100 mg/mL. In certain embodiments, the concentration of furosemide in the liquid pharmaceutical formulation is greater than about 5 mg/mL. In certain embodiments, the concentration of furosemide in the liquid pharmaceutical formulation is greater than about 20 mg/mL.

In various embodiments, the concentration of furosemide in the liquid pharmaceutical formulations described herein can be about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL.

In various embodiments, the liquid pharmaceutical formulations described herein further comprise a pharmaceutically acceptable pH adjuster. In certain embodiments, the pharmaceutically acceptable pH adjuster is selected from the group comprising acetic acid, citric acid, fumaric acid, hydrochloric acid, malic acid, nitric acid, phosphoric acid, propionic acid, sulfuric acid, tartaric acid, ammonia solution, ammonium carbonate, diethanolamine, potassium hydroxide, sodium bicarbonate, sodium borate, sodium carbonate, sodium hydroxide, trolamine or any combination thereof. In certain embodiments, the pharmaceutically acceptable pH adjuster is sodium hydroxide or hydrochloric acid.

In various embodiments, the liquid pharmaceutical formulations described herein further comprise an osmolarity adjuster. In some embodiments, the osmolarity adjuster is selected from the group comprising sodium chloride, potassium chloride, isosorbide, mannitol, xylitol or any combination thereof. In certain embodiments, the osmolarity adjuster is sodium chloride.

In various embodiments, the liquid pharmaceutical formulations described herein may further comprise one or more additional pharmaceutically acceptable carriers, excipients, or diluents. Examples of liquid carriers for parenteral administration include water, alcohols (including monohydric alcohols and polyhydric alcohols, e.g., glycols) and their derivatives, and oils (e.g., fractionated coconut oil and *arachis* oil). In some embodiments, the carrier is an oily ester such as ethyl oleate and isopropyl myristate. Examples of such carriers are well known to those skilled in the art and can be prepared in accordance with acceptable pharmaceutical procedures, such as, for example, those described in Remington: The Science and Practice of Pharmacy, 20th edition, ed. Alfonso R. Gennaro (Lippincott Williams & Wilkins, Baltimore, Md. (2000)). For example, liquid media or liquid carriers (which are used interchangeably herein) can be used in preparing the liquid pharmaceutical formulations described herein such as solutions, suspensions, and emulsions. In certain embodiments, the pharmaceutically acceptable carrier is a sterile carrier.

In certain embodiments, the liquid pharmaceutical formulation comprises one of more of water; a pH adjuster; and an osmolarity adjuster. In particular embodiments, the pH adjuster is selected from the group consisting of potassium hydroxide, sodium hydroxide, hydrochloric acid, and combinations thereof. In some embodiments, the osmolarity adjuster is selected from the group consisting of sodium chloride, potassium chloride, and combinations thereof.

In various embodiments, the liquid pharmaceutical formulations described herein may further comprise other suitable pharmaceutically acceptable additives such as solubilizers, emulsifiers, buffers, preservatives, sweeteners, flavoring agents, suspending agents, thickening agents, colors, viscosity regulators, stabilizers, and osmo-regulators.

In various embodiments, the liquid pharmaceutical formulations described herein further comprise a second therapeutic agent. In certain embodiments, furosemide is the sole therapeutic agent present in the liquid pharmaceutical formulations described herein.

In various embodiments, the liquid pharmaceutical formulations described herein have an osmolarity in the range of from about 100 mOsm/kg to about 1600 mOsm/kg, from about 200 mOsm/kg to about 1600 mOsm/kg, from about 400 mOsm/kg to about 1600 mOsm/kg, from about 800 mOsm/kg to about 1600 mOsm/kg, from about 1200 mOsm/kg to about 1600 mOsm/kg, from about 100 mOsm/kg to about 1200 mOsm/kg, from about 100 mOsm/kg to about 800 mOsm/kg, from about 100 mOsm/kg to about 400 mOsm/kg, from about 100 mOsm/kg to about 200 mOsm/kg, from about 200 mOsm/kg to about 1200 mOsm/kg, from about 200 mOsm/kg to about 800 mOsm/kg, from about 200 mOsm/kg to about 400 mOsm/kg, from about 400 mOsm/kg to about 1200 mOsm/kg, from about 400 mOsm/kg to about 800 mOsm/kg, or from about 800 mOsm/kg to about 1200 mOsm/kg. In some embodiments, the liquid pharmaceutical formulations described herein have an osmolarity in the range of from about 200 mOsm/kg to about 400 mOsm/kg.

In certain embodiments, the liquid pharmaceutical formulations described herein have an osmolarity in the range of from about 275 mOsm/kg to about 350 mOsm/kg. In certain embodiments, the liquid pharmaceutical formulations described herein are isosmotic.

Unit Liquid Pharmaceutical Formulations of Furosemide

As described herein, in one aspect, the invention provides unit liquid pharmaceutical formulations of furosemide or a pharmaceutically acceptable salt thereof.

In various embodiments, a unit liquid pharmaceutical formulation generally comprises:
 (i) furosemide, or a pharmaceutically acceptable salt thereof;
 (ii) one or more pharmaceutically acceptable excipients; and
 (iii) a pharmaceutically acceptable buffer.

In various embodiments, the one or more pharmaceutically acceptable excipients is selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof. In certain embodiments, the PEG has a weight average molecular weight of from about 3000 g/mol to about 3700 g/mol. In certain embodiments, the polysorbate is polysorbate 80. In certain embodiments, the PVP has a weight average molecular weight of about 4000 g/mol to about 6000 g/mol. In certain embodiments, the cyclodextrin is β-cyclodextrin.

In certain embodiments, the amount of the one or more pharmaceutically acceptable excipients in the unit liquid pharmaceutical formulations described herein can be from about 0.1% (w/w) to about 30% (w/w), from about 0.5% (w/w) to about 30% (w/w), from about 1% (w/w) to about 30% (w/w), from about 1.5% (w/w) to about 30% (w/w), (w/w), from about 2% (w/w) to about 30% (w/w), from about 2.5% (w/w) to about 30% (w/w), from about 3% (w/w) to about 30% (w/w), from about 3.5% (w/w) to about 30% (w/w), from about 4% (w/w) to about 30% (w/w), from about 4.5% (w/w) to about 30% (w/w), from about 5% (w/w) to about 30% (w/w), from about 10% (w/w) to about 30% (w/w), from about 15% (w/w) to about 30% (w/w), from about 20% (w/w) to about 30% (w/w), from about 25% (w/w) to about 30% (w/w), from about 0.1% (w/w) to about 25% (w/w), from about 0.1% (w/w) to about 20% (w/w), from about 0.1% (w/w) to about 15% (w/w), from about 0.1% (w/w) to about 10% (w/w), from about 0.1% (w/w) to about 5% (w/w), from about 0.1% (w/w) to about 4.5% (w/w), from about 0.1% (w/w) to about 4% (w/w), from about 0.1% (w/w) to about 3.5% (w/w), from about 0.1% (w/w) to about 3% (w/w), from about 0.1% (w/w) to about 2.5% (w/w), from about 0.1% (w/w) to about 2% (w/w), from about 0.1% (w/w) to about 1.5% (w/w), from about 0.1% (w/w) to about 1% (w/w), from about 0.1% (w/w) to about 0.5% (w/w), from about 0.5% (w/w) to about 25% (w/w), from about 0.5% (w/w) to about 20% (w/w), from about 0.5% (w/w) to about 15% (w/w), from about 0.5% (w/w) to about 10% (w/w), from about 0.5% (w/w) to about 5% (w/w), from about 0.5% (w/w) to about 4.5% (w/w), from about 0.5% (w/w) to about 4% (w/w), from about 0.5% (w/w) to about 3.5% (w/w), from about 0.5% (w/w) to about 3% (w/w), from about 0.5% (w/w) to about 2.5% (w/w), from about 0.5% (w/w) to about 2% (w/w), from about 0.5% (w/w) to about 1.5% (w/w), from about 0.5% (w/w) to about 1% (w/w), from about 1% (w/w) to about 25% (w/w), from about 1% (w/w) to about 20% (w/w), from about 1% (w/w) to about 15% (w/w), from about 1% (w/w) to about 10% (w/w), from about 1% (w/w) to about 5% (w/w), from about 1% (w/w) to about 4.5% (w/w), from about 1% (w/w) to about 4% (w/w), from about 1% (w/w) to about 3.5% (w/w), from about 1% (w/w) to about 2.5% (w/w), from about 1% (w/w) to about 2% (w/w), from about 1% (w/w) to about 1.5% (w/w), from about 1.5% (w/w) to about 25% (w/w), from about 1.5% (w/w) to about 20% (w/w), from about 1.5% (w/w) to about 15% (w/w), from about 1.5% (w/w) to about 10% (w/w), from about 1.5% (w/w) to about 5% (w/w), from about 1.5% (w/w) to about 4.5% (w/w), from about 1.5% (w/w) to about 4% (w/w), from about 1.5% (w/w) to about 3.5% (w/w), from about 1.5% (w/w) to about 3% (w/w), from about 1.5% (w/w) to about 2.5% (w/w), from about 1.5% (w/w) to about 2% (w/w), from about 2% (w/w) to about 25% (w/w), from about 2% (w/w) to about 20% (w/w), from about 2% (w/w) to about 15% (w/w), from about 2% (w/w) to about 10% (w/w), from about 2% (w/w) to about 5% (w/w), from about 2% (w/w) to about 4.5% (w/w), from about 2% (w/w) to about 4% (w/w), from about 2% (w/w) to about 3.5% (w/w), from about 2% (w/w) to about 3% (w/w), from about 2% (w/w) to about 2.5% (w/w), from about 2.5% (w/w) to about 25% (w/w), from about 2.5% (w/w) to about 20% (w/w), from about 2.5% (w/w) to about 15% (w/w), from about 2.5% (w/w) to about 10% (w/w), from about 2.5% (w/w) to about 5% (w/w), from about 2.5% (w/w) to about 4.5% (w/w), from about 2.5% (w/w) to about 4% (w/w), from about 2.5% (w/w) to about 3.5% (w/w), from about 2.5% (w/w) to about 3% (w/w), from about 3% (w/w) to about 25% (w/w), from about 3% (w/w) to about 20% (w/w), from about 3% (w/w) to about 15% (w/w), from about 3% (w/w) to about 10% (w/w), from about 3% (w/w) to about 5% (w/w), from about 3% (w/w) to about 4.5% (w/w), from about 3% (w/w) to about 4% (w/w), from about 3% (w/w) to about 3.5% (w/w), from about 3.5% (w/w) to about 25% (w/w), from about 3.5% (w/w) to about 20% (w/w), from about 3.5% (w/w) to about 15% (w/w), from about 3.5% (w/w) to about 10% (w/w), from about 3.5% (w/w) to about 5% (w/w), from about 3.5% (w/w) to about 4.5% (w/w), from about 3.5% (w/w) to about 4% (w/w), from about 4% (w/w) to about 25% (w/w), from about 4% (w/w) to about 20% (w/w), from about 4% (w/w) to about 15% (w/w), from about 4% (w/w) to about 10% (w/w), from about 4% (w/w) to about 5% (w/w), from about 4% (w/w) to about 4.5% (w/w), from about 4.5% (w/w) to about 25% (w/w), from about 4.5% (w/w) to about 20% (w/w), from about 4.5% (w/w) to about 15% (w/w), from about 4.5% (w/w) to about 10% (w/w), from about 4.5% (w/w) to about 5% (w/w), from about 5% (w/w) to about 25% (w/w), from about 5% (w/w) to about 20% (w/w), from about 5% (w/w) to about 15% (w/w), from about 5% (w/w) to about 10% (w/w), from about 10% (w/w) to about 25% (w/w), from about 10% (w/w) to about 20% (w/w), from about 10% (w/w) to about 15% (w/w), from about 15% (w/w) to about 25% (w/w), from about 15% (w/w) to about 20% (w/w), or from about 20% (w/w) to about 25% (w/w). In certain embodiments, the amount of the one or more pharmaceutically acceptable excipients in the unit liquid pharmaceutical formulation is from about 1.5% (w/w) to about 30% (w/w). In certain embodiments, the amount of the one or more pharmaceutically acceptable excipients in the unit liquid pharmaceutical formulation is from about 5% (w/w) to about 15% (w/w). In certain embodiments, the amount of the one or more pharmaceutically acceptable excipients in the unit liquid pharmaceutical formulation is from about 0.1% (w/w) to about 10% (w/w). In certain embodiments, the amount of the one or more pharmaceutically acceptable excipients in the unit liquid pharmaceutical formulation is from about 0.5% (w/w) to about 5% (w/w).

In various embodiments, the amount of the one or more pharmaceutically acceptable excipients in the unit liquid pharmaceutical formulations described herein can about 0.1% (w/w), about 0.25% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21% (w/w), about 22% (w/w), about 23% (w/w), about 24% (w/w), about 25% (w/w), about 26% (w/w), about 27% (w/w), about 28% (w/w), about 29% (w/w), or about 30% (w/w).

In certain embodiments, the one or more pharmaceutically acceptable excipients comprises benzyl alcohol. In certain embodiments, the one or more pharmaceutically acceptable excipients comprises NMP. In certain embodiments, the one or more pharmaceutically acceptable excipients comprises NMP and benzyl alcohol.

In various embodiments, the concentration of the pharmaceutically acceptable buffer in the unit liquid pharmaceutical formulations described herein can be from about 25 mM to about 500 mM, from about 30 mM to about 500 mM, from about 40 mM to about 500 mM, from about 50 mM to about 500 mM, from about 75 mM to about 500 mM, from about 100 mM to about 500 mM, from about 150 mM to about 500 mM, from about 200 mM to about 500 mM, from about 200 mM to about 500 mM, from about 250 mM to about 500 mM, from about 300 mM to about 500 mM, from about 350 mM to about 500 mM, from about 400 mM to about 500 mM, from about 450 mM to about 500 mM, from about 25 mM to about 450 mM, from about 25 mM to about 400 mM, from about 25 mM to about 350 mM, from about 25 mM to about 300 mM, from about 25 mM to about 250 mM, from about 25 mM to about 200 mM, from about 25 mM to about 150 mM, from about 25 mM to about 100 mM, from about 25 mM to about 75 mM, from about 25 mM to about 50 mM, from about 25 mM to about 40 mM, from about 25 mM to about 30 mM, from about 30 mM to about 450 mM, from about 30 mM to about 400 mM, from about 30 mM to about 350 mM, from about 30 mM to about 300 mM, from about 30 mM to about 250 mM, from about 30 mM to about 200 mM, from about 30 mM to about 150 mM, from about 30 mM to about 100 mM, from about 30 mM to about 75 mM, from about 30 mM to about 50 mM, from about 30 mM to about 40 mM, from about 40 mM to about 450 mM, from about 40 mM to about 400 mM, from about 40 mM to about 350 mM, from about 40 mM to about 300 mM, from about 40 mM to about 250 mM, from about 40 mM to about 200 mM, from about 40 mM to about 150 mM, from about 40 mM to about 100 mM, from about 40 mM to about 75 mM, from about 40 mM to about 50 mM, from about 50 mM to about 450 mM, from about 50 mM to about 400 mM, from about 50 mM to about 350 mM, from about 50 mM to about 300 mM, from about 50 mM to about 250 mM, from about 50 mM to about 200 mM, from about 50 mM to about 150 mM, from about 50 mM to about 100 mM, from about 50 mM to about 75 mM, from about 75 mM to about 450 mM, from about 75 mM to about 400 mM, from about 75 mM to about 350 mM, from about 75 mM to about 300 mM, from about 75 mM to about 250 mM, from about 75 mM to about 200 mM, from about 75 mM to about 150 mM, from about 75 mM to about 100 mM, from about 100 mM to about 450 mM, from about 100 mM to about 400 mM, from about 100 mM to about 350 mM, from about 100 mM to about 300 mM, from about 100 mM to about 250 mM, from about 100 mM to about 200 mM, from about 100 mM to about 150 mM, from about 150 mM to about 450 mM, from about 150 mM to about 400 mM, from about 150 mM to about 350 mM, from about 150 mM to about 300 mM, from about 150 mM to about 250 mM, from about 150 mM to about 200 mM, from about 200 mM to about 450 mM, from about 200 mM to about 400 mM, from about 200 mM to about 350 mM, from about 200 mM to about 300 mM, from about 200 mM to about 250 mM, from about 250 mM to about 450 mM, from about 250 mM to about 400 mM, from about 250 mM to about 350 mM, from about 250 mM to about 300 mM, from about 300 mM to about 450 mM, from about 300 mM to about 400 mM, from about 300 mM to about 350 mM, from about 350 mM to about 450 mM, from about 350 mM to about 400 mM, or from about 400 mM to about 450 mM. In certain embodiments, the concentration of the pharmaceutically acceptable buffer in the unit liquid pharmaceutical formulation is from about 25 mM to about 250 mM. In certain embodiments, the concentration of the pharmaceutically acceptable buffer in the unit liquid pharmaceutical formulation is from about 25 mM to about 100 mM.

In various embodiments, the pharmaceutically acceptable buffer comprises a buffering agent selected from the group consisting of histidine, a citrate salt, sodium phosphate, potassium phosphate, tromethamine or a pharmaceutically acceptable salt thereof, and any combination thereof.

In certain embodiments, the buffering agent is tromethamine or a pharmaceutically acceptable salt thereof.

In various embodiments, a unit liquid pharmaceutical formulation comprises:
   (i) furosemide, or a pharmaceutically acceptable salt thereof;
   (ii) benzyl alcohol; and
   (iii) tromethamine or a pharmaceutically acceptable salt thereof.

In certain embodiments, the unit liquid pharmaceutical formulations further comprise N-methyl-pyrrolidone (NMP).

In various embodiments, a unit liquid pharmaceutical formulation comprises:
   (i) furosemide, or a pharmaceutically acceptable salt thereof;
   (ii) N-methyl-pyrrolidone (NMP);
   (iii) benzyl alcohol; and
   (iv) tromethamine or a pharmaceutically acceptable salt thereof.

In various embodiments, the amount of furosemide, or a pharmaceutically acceptable salt thereof, in the unit liquid pharmaceutical formulations described herein can be from about 20 mg to about 200 mg, from about 40 mg to about 200 mg, from about 60 mg to about 200 mg, from about 80 mg to about 200 mg, from about 100 mg to about 200 mg, from about 120 mg to about 200 mg, from about 140 mg to about 200 mg, from about 160 mg to about 200 mg, from about 180 mg to about 200 mg, from about 20 mg to about 180 mg, from about 20 mg to about 160 mg, from about 20 mg to about 140 mg, from about 20 mg to about 120 mg, from about 20 mg to about 100 mg, from about 20 mg to about 80 mg, from about 20 mg to about 60 mg, from about 20 mg to about 40 mg, from about 40 mg to about 180 mg, from about 40 mg to about 160 mg, from about 40 mg to about 140 mg, from about 40 mg to about 120 mg, from about 40 mg to about 100 mg, from about 40 mg to about 80 mg, from about 40 mg to about 60 mg, from about 60 mg to about 180 mg, from about 60 mg to about 160 mg, from about 60 mg to about 140 mg, from about 60 mg to about 120 mg, from about 60 mg to about 100 mg, from about 60 mg to about 80 mg, from about 80 mg to about 180 mg, from about 80 mg to about 160 mg, from about 80 mg to about 140 mg, from about 80 mg to about 120 mg, from about 80 mg to about 100 mg, from about 100 mg to about 180 mg, from about 100 mg to about 160 mg, from about 100 mg to about 140 mg, from about 100 mg to about 120 mg, from about 120 mg to about 180 mg, from about 120 mg to about 160 mg, from about 120 mg to about 140 mg, from about 140 mg to about 180 mg, from about 140 mg to about 160 mg, or from about 160 mg to about 180 mg. In certain embodiments, the amount of furosemide, or a pharmaceutically acceptable salt thereof, in the unit liquid pharmaceutical formulations is from about 20 mg to about 200 mg, from about 40 mg to about 200 mg, from about 60 mg to about 200 mg, or from about 80 mg to about 200 mg. In some embodiments, the amount of furosemide, or a pharmaceutically acceptable salt thereof, in the unit liquid pharmaceutical formulation is from about 80 mg to about 200 mg.

In various embodiments, the unit liquid pharmaceutical formulations described herein comprise about 10 mg, about 20 mg, about 30 mg, about 40 mg, about 50 mg, about 60 mg, about 70 mg, about 80 mg, about 90 mg, about 100 mg, about 120 mg, about 130 mg, about 140 mg, about 150 mg, about 160 mg, about 170 mg, about 180 mg, about 190 mg, or about 200 mg of furosemide, or a pharmaceutically acceptable salt thereof.

In various embodiments, the amount of benzyl alcohol in the unit liquid pharmaceutical formulations described herein can be from about 0.1% (w/w) to about 10% (w/w), from about 0.5% (w/w) to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 0.1% (w/w) to about 5% (w/w), from about 0.1% (w/w) to about 4% (w/w), from about 0.1% (w/w) to about 3% (w/w), from about 0.1% (w/w) to about 2% (w/w), from about 0.1% (w/w) to about 1% (w/w), from about 0.1% (w/w) to about 0.5% (w/w), from about 0.5% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 5% (w/w), from about 2% (w/w) to about 4% (w/w), from about 2% (w/w) to about 3% (w/w), from about 3% (w/w) to about 5% (w/w), from about 3% (w/w) to about 4% (w/w), or from about 4% (w/w) to about 5% (w/w). In certain embodiments, the amount of benzyl alcohol in the unit liquid pharmaceutical formulation is from about 0.1% (w/w) to about 10% (w/w). In certain embodiments, the amount of benzyl alcohol in the unit liquid pharmaceutical formulation is from about 0.5% (w/w) to about 5% (w/w).

In various embodiments, the amount of benzyl alcohol in the unit liquid pharmaceutical formulations described herein can be about 0.1% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 6% (w/w), about 7% (w/w), about 8% (w/w), about 9% (w/w), or about 10% (w/w). In certain embodiments, the amount of benzyl alcohol in the unit liquid pharmaceutical formulation is about 4% (w/w).

In various embodiments, a unit liquid pharmaceutical formulation comprises:
   (i) from about 10 mg to about 200 mg furosemide, or a pharmaceutically acceptable salt thereof;
   (ii) from about 0.1% (w/w) to about 10% (w/w) benzyl alcohol; and
   (iii) from about 25 mM to about 250 mM tromethamine or a pharmaceutically acceptable salt thereof,
wherein the concentration of furosemide in the unit liquid pharmaceutical formulation is from about 40 mg/mL to about 250 mg/mL.

In certain embodiments, the unit liquid pharmaceutical formulations further comprise N-methyl-pyrrolidone (NMP).

In various embodiments, the amount of NMP in the unit liquid pharmaceutical formulations described herein can be from about 0.1% (w/w) to about 10% (w/w), from about 0.5% (w/w) to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 0.1% (w/w) to about 5% (w/w), from about 0.1% (w/w) to about 4% (w/w), from about 0.1% (w/w) to about 3% (w/w), from about 0.1% (w/w) to about 2% (w/w), from about 0.1% (w/w) to about 1% (w/w), from about 0.1% (w/w) to about 0.5% (w/w), from about 0.5% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 5% (w/w), from about 2% (w/w) to about 4% (w/w), from about 2% (w/w) to about 3% (w/w), from about 3% (w/w) to about 5% (w/w), from about 3% (w/w) to about 4% (w/w), or from about 4% (w/w) to about 5% (w/w). In certain embodiments, the amount of NMP in the unit liquid pharmaceutical formulation is from about 0.1% (w/w) to about 10% (w/w). In certain embodiments, the amount of NMP in the unit liquid pharmaceutical formulation is from about 0.1% (w/w) to about 1% (w/w).

In various embodiments, the amount of NMP in the unit liquid pharmaceutical formulations described herein can be about 0.1% (w/w), about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), or about 10% (w/w). In some embodiments, the amount of NMP in the unit liquid pharmaceutical formulation is about 0.5 (w/w).

In various embodiments, a unit liquid pharmaceutical formulation comprises:
 (i) from about 10 mg to about 200 mg furosemide, or a pharmaceutically acceptable salt thereof;
 (ii) from about 0.1% (w/w) to about 10% (w/w) benzyl alcohol;
 (iii) from about 0.1% (w/w) to about 10% (w/w) N-methyl-pyrrolidone (NMP); and
 (iv) from about 25 mM to about 250 mM tromethamine or a pharmaceutically acceptable salt thereof,
wherein the concentration of furosemide in the unit liquid pharmaceutical formulation is from about 40 mg/mL to about 250 mg/mL.

In various embodiments, a unit liquid pharmaceutical formulation comprises:
 (i) from about 10 mg to about 200 mg furosemide, or a pharmaceutically acceptable salt thereof;
 (ii) N-methyl-pyrrolidone (NMP); and
 (iii) a pharmaceutically acceptable buffer,
wherein the concentration of furosemide in the unit liquid pharmaceutical formulation is from about 40 mg/mL to about 250 mg/mL.

In various embodiments, the amount of NMP in the unit liquid pharmaceutical formulations described herein can be from about 1% (w/w) to about 25% (w/w), from about 2.5% (w/w) to about 25% (w/w), from about 5% (w/w) to about 25% (w/w), from about 7.5% (w/w) to about 25% (w/w), from about 10% (w/w) to about 25% (w/w), from about 12.5% (w/w) to about 25% (w/w), from about 15% (w/w) to about 25% (w/w), from about 20% (w/w) to about 25% (w/w), from about 1% (w/w) to about 20% (w/w), from about 1% (w/w) to about 15% (w/w), from about 1% (w/w) to about 12.5% (w/w), from about 1% (w/w) to about 10% (w/w), from about 1% (w/w) to about 7.5% (w/w), from about 1% (w/w) to about 5% (w/w), from about 1% (w/w) to about 2.5% (w/w), from about 2.5% (w/w) to about 20% (w/w), from about 2.5% (w/w) to about 15% (w/w), from about 2.5% (w/w) to about 12.5% (w/w), from about 2.5% (w/w) to about 10% (w/w), from about 2.5% (w/w) to about 7.5% (w/w), from about 2.5% (w/w) to about 5% (w/w), from about 5% (w/w) to about 20% (w/w), from about 5% (w/w) to about 15% (w/w), from about 5% (w/w) to about 12.5% (w/w), from about 5% (w/w) to about 10% (w/w), from about 5% (w/w) to about 7.5% (w/w), from about 7.5% (w/w) to about 20% (w/w), from about 7.5% (w/w) to about 15% (w/w), from about 7.5% (w/w) to about 12.5% (w/w), from about 7.5% (w/w) to about 10% (w/w), from about 10% (w/w) to about 20% (w/w), from about 10% (w/w) to about 15% (w/w), from about 10% (w/w) to about 12.5% (w/w), from about 12.5% (w/w) to about 20% (w/w), from about 12.5% (w/w) to about 15% (w/w), from about 12.5% (w/w) to about 20% (w/w), from about 12.5% (w/w) to about 15% (w/w), or from about 15% (w/w) to about 20% (w/w). In certain embodiments, the amount of NMP in the unit liquid pharmaceutical formulation is from about 1% (w/w) to about 25% (w/w). In certain embodiments, the amount of NMP in the unit liquid pharmaceutical formulation is from about 5% (w/w) to about 10% (w/w).

In various embodiments, the amount of NMP in the unit liquid pharmaceutical formulations described herein can be about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 12.5% (w/w), about 15% (w/w), about 20% (w/w), or about 25% (w/w).

In certain embodiments, the unit liquid pharmaceutical formulation further comprises benzyl alcohol.

In various embodiments, the amount of benzyl alcohol in the unit liquid pharmaceutical formulations described herein can be from about 0.5% (w/w) to about 5% (w/w), from about 1% (w/w) to about 5% (w/w), from about 2% (w/w) to about 5% (w/w), from about 3% (w/w) to about 5% (w/w), from about 4% (w/w) to about 5% (w/w), from about 0.5% (w/w) to about 4% (w/w), from about 0.5% (w/w) to about 3% (w/w), from about 0.5% (w/w) to about 2% (w/w), from about 0.5% (w/w) to about 1% (w/w), from about 1% (w/w) to about 4% (w/w), from about 1% (w/w) to about 3% (w/w), from about 1% (w/w) to about 2% (w/w), from about 2% (w/w) to about 4% (w/w), from about 2% (w/w) to about 3% (w/w), or from about 3% (w/w) to about 4% (w/w). In certain embodiments, the amount of benzyl alcohol in the unit liquid pharmaceutical formulation is from about 0.5% (w/w) to about 5% (w/w). In certain embodiments, the amount of benzyl alcohol in the unit liquid pharmaceutical formulation is from about 1% (w/w) to about 3% (w/w).

In various embodiments, the amount of benzyl alcohol in the unit liquid pharmaceutical formulations described herein can be about 0.5% (w/w), about 1% (w/w), about 1.5% (w/w), about 2% (w/w), about 2.5% (w/w), about 3% (w/w), about 3.5% (w/w), about 4% (w/w), about 4.5% (w/w), or about 5% (w/w).

In some embodiments, the pharmaceutically acceptable salt of tromethamine is tromethamine hydrochloride.

In various embodiments, a unit liquid pharmaceutical formulation comprises:
(i) from about 10 mg to about 200 mg furosemide, or a pharmaceutically acceptable salt thereof;
(ii) from about 0.1% (w/w) to about 30% (w/w) of one or more pharmaceutically acceptable excipients selected from the group consisting of ethanol, benzyl alcohol, glycerin, N-methyl-pyrrolidone (NMP), sodium chloride, a polyethylene glycol (PEG), propylene glycol, a polysorbate, a polyvinylpyrrolidone (PVP), a cyclodextrin, and any combination thereof; and
(iii) from about 25 mM to about 500 mM of a pharmaceutically acceptable buffer selected from the group consisting of histidine, a citrate salt, sodium phosphate, potassium phosphate, tromethamine or a pharmaceutically acceptable salt thereof, and any combination thereof,
wherein the concentration of furosemide in the liquid pharmaceutical formulation is from about 40 mg/mL to about 250 mg/mL and the pH of the liquid pharmaceutical formulation is from about 6.5 to about 8.5.

In various embodiments, a unit liquid pharmaceutical formulation comprises:
(i) from about 10 mg to about 200 mg furosemide, or a pharmaceutically acceptable salt thereof;
(ii) from about 0.1% (w/w) to about 10% (w/w) benzyl alcohol;
(iii) from about 25 mM to about 250 mM tromethamine or a pharmaceutically acceptable salt thereof,
wherein the concentration of furosemide in the unit liquid pharmaceutical formulation is from about 40 mg/mL to about 250 mg/mL.

In various embodiments, a unit liquid pharmaceutical formulation comprises:
(i) from about 10 mg to about 200 mg furosemide, or a pharmaceutically acceptable salt thereof;
(ii) from about 0.1% (w/w) to about 10% (w/w) benzyl alcohol;
(iii) from about 0.1% (w/w) to about 10% (w/w) N-methyl-pyrrolidone (NMP);
(iv) from about 25 mM to about 250 mM tromethamine or a pharmaceutically acceptable salt thereof,
wherein the concentration of furosemide in the unit liquid pharmaceutical formulation is from about 40 mg/mL to about 250 mg/mL.

In various embodiments, a unit liquid pharmaceutical formulation comprises:
(i) from about 10 mg to about 200 mg furosemide, or a pharmaceutically acceptable salt thereof;
(ii) from about 1% (w/w) to about 25% (w/w) N-methyl-pyrrolidone (NMP);
(iii) from about 0.5% (w/w) to about 5% (w/w) benzyl alcohol; and
(iv) from about 25 mM to about 250 mM tromethamine or a pharmaceutically acceptable salt thereof,
wherein the concentration of furosemide in the unit liquid pharmaceutical formulation is from about 40 mg/mL to about 250 mg/mL.

In various embodiments, the concentration of tromethamine or a pharmaceutically acceptable salt thereof in the unit liquid pharmaceutical formulations described herein can be from about 25 mM to about 250 mM, from about 50 mM to about 250 mM, from about 75 mM to about 250 mM, from about 100 mM to about 250 mM, from about 125 mM to about 250 mM, from about 150 mM to about 250 mM, from about 175 mM to about 250 mM, from about 200 mM to about 250 mM, from about 225 mM to about 250 mM, from about 25 mM to about 225 mM, from about 25 mM to about 200 mM, from about 25 mM to about 175 mM, from about 25 mM to about 150 mM, from about 25 mM to about 125 mM, from about 25 mM to about 100 mM, from about 25 mM to about 75 mM, from about 25 mM to about 50 mM, from about 50 mM to about 225 mM, from about 50 mM to about 200 mM, from about 50 mM to about 175 mM, from about 50 mM to about 150 mM, from about 50 mM to about 125 mM, from about 50 mM to about 100 mM, from about 50 mM to about 75 mM, from about 75 mM to about 225 mM, from about 75 mM to about 200 mM, from about 75 mM to about 175 mM, from about 75 mM to about 150 mM, from about 75 mM to about 125 mM, from about 75 mM to about 100 mM, from about 100 mM to about 225 mM, from about 100 mM to about 200 mM, from about 100 mM to about 175 mM, from about 100 mM to about 150 mM, from about 100 mM to about 125 mM, from about 125 mM to about 225 mM, from about 125 mM to about 200 mM, from about 125 mM to about 175 mM, from about 125 mM to about 150 mM, from about 150 mM to about 225 mM, from about 150 mM to about 200 mM, from about 150 mM to about 175 mM, from about 150 mM to about 250 mM, from about 175 mM to about 225 mM, from about 175 mM to about 200 mM, or from about 200 mM to about 225 mM. In certain embodiments, the concentration of tromethamine or a pharmaceutically acceptable salt thereof in the unit liquid pharmaceutical formulation is from about 25 mM to about 250 mM. In certain embodiments, the concentration of tromethamine or a pharmaceutically acceptable salt thereof in the unit liquid pharmaceutical formulation is from about 25 mM to about 100 mM.

In various embodiments, the concentration of tromethamine or a pharmaceutically acceptable salt thereof in the unit liquid pharmaceutical formulations described herein can be about 25 mM, about 50 mM, about 75 mM, about 100 mM, about 125 mM, about 150 mM, about 175 mM, about 200 mM, about 225 mM, or about 250 mM. In certain embodiments, the concentration of tromethamine or a pharmaceutically acceptable salt thereof in the unit liquid pharmaceutical formulation is about 50 mM.

In various embodiments, the concentration of furosemide in the unit liquid pharmaceutical formulations described herein can be from about 50 mg/mL to about 250 mg/mL, from about 60 mg/mL to about 250 mg/mL, from about 70 mg/mL to about 250 mg/mL, from about 80 mg/mL to about 250 mg/mL, from about 90 mg/mL to about 250 mg/mL, from about 100 mg/mL to about 250 mg/mL, from about 120 mg/mL to about 250 mg/mL, from about 140 mg/mL to about 250 mg/mL, from about 160 mg/mL to about 250 mg/mL, from about 180 mg/mL to about 250 mg/mL, from about 200 mg/mL to about 250 mg/mL, from about 50 mg/mL to about 200 mg/mL, from about 50 mg/mL to about 180 mg/mL, from about 50 mg/mL to about 160 mg/mL, from about 50 mg/mL to about 140 mg/mL, from about 50 mg/mL to about 120 mg/mL, from about 50 mg/mL to about 100 mg/mL, from about 50 mg/mL to about 90 mg/mL, from about 50 mg/mL to about 80 mg/mL, from about 50 mg/mL to about 70 mg/mL, from about 50 mg/mL to about 60 mg/mL, from about 60 mg/mL to about 200 mg/mL, from about 60 mg/mL to about 180 mg/mL, from about 60 mg/mL to about 160 mg/mL, from about 60 mg/mL to about 140 mg/mL, from about 60 mg/mL to about 120 mg/mL, from about 60 mg/mL to about 100 mg/mL, from about 60 mg/mL to about 90 mg/mL, from about 60 mg/mL to about 80 mg/mL, from about 60 mg/mL to about 70 mg/mL, from about 70 mg/mL to about 200 mg/mL, from about 70 mg/mL to about 180 mg/mL, from about 70 mg/mL to about 160 mg/mL, from about 70 mg/mL to about 140 mg/mL, from about 70 mg/mL to about 120 mg/mL, from about 70 mg/mL to about 100 mg/mL, from about 70 mg/mL to about 90 mg/mL, from about 70 mg/mL to about 80 mg/mL, from about 80 mg/mL to about 200 mg/mL, from about 80 mg/mL to about 180 mg/mL, from about 80 mg/mL to about 160 mg/mL, from about 80 mg/mL to about 140 mg/mL, from about 80 mg/mL to about 120 mg/mL, from about 80 mg/mL to about 100 mg/mL, from about 80 mg/mL to about 90 mg/mL, from about 90 mg/mL to about 200 mg/mL, from about 90 mg/mL to about 180 mg/mL, from about 90 mg/mL to about 160 mg/mL, from about 90 mg/mL to about 140 mg/mL, from about 90 mg/mL to about 120 mg/mL, from about 90 mg/mL to about 100 mg/mL, from about 100 mg/mL to about 200 mg/mL, from about 100 mg/mL to about 180 mg/mL, from about 100 mg/mL to about 160 mg/mL, from about 100 mg/mL to about 140 mg/mL, from about 100 mg/mL to about 120 mg/mL, from about 120 mg/mL to about 200 mg/mL, from about 120 mg/mL to about 180 mg/mL, from about 120 mg/mL to about 160 mg/mL, from about 120 mg/mL to about 140 mg/mL, from about 140 mg/mL to about 200 mg/mL, from about 140 mg/mL to about 180 mg/mL, from about 140 mg/mL to about 160 mg/mL, from about 160 mg/mL to about 200 mg/mL, from about 160 mg/mL to about 180 mg/mL, or from about 180 mg/mL to about 200 mg/mL. In certain embodiments, the concentration of furosemide in the unit liquid pharmaceutical formulation is from about 50 mg/mL to about 250 mg/mL, from about 60 mg/mL to about 250 mg/mL, from about 70 mg/mL to about 250 mg/mL, or from about 80 mg/mL to about 250 mg/mL. In certain embodiments, the concentration of furosemide in the unit liquid pharmaceutical formulation is from about 80 mg/mL to about 250 mg/mL.

In various embodiments, the concentration of furosemide in the unit liquid pharmaceutical formulations described herein can be greater than about 40 mg/mL, greater than about 50 mg/mL, greater than about 60 mg/mL, greater than about 70 mg/mL, greater than about 80 mg/mL, greater than about 90 mg/mL, greater than about 100 mg/mL, greater than about 120 mg/mL, greater than about 140 mg/mL, greater than about 160 mg/mL, greater than about 180 mg/mL, greater than about 200 mg/mL, greater than about 220 mg/mL, or greater than about 250 mg/mL. In certain embodiments, the concentration of furosemide in the unit liquid pharmaceutical formulation is greater than about 40 mg/mL. In certain embodiments, the concentration of furosemide in the unit liquid pharmaceutical formulation is greater than about 50 mg/mL. In certain embodiments, the concentration of furosemide in the unit liquid pharmaceutical formulation is greater than about 60 mg/mL. In certain embodiments, the concentration of furosemide in the unit liquid pharmaceutical formulation is greater than about 70 mg/mL. In certain embodiments, the concentration of furosemide in the unit liquid pharmaceutical formulation is greater than about 80 mg/mL.

In various embodiments, the concentration of furosemide in the unit liquid pharmaceutical formulations described herein can be about 40 mg/mL, about 50 mg/mL, about 60 mg/mL, about 70 mg/mL, about 80 mg/mL, about 90 mg/mL, about 100 mg/mL, about 120 mg/mL, about 140 mg/mL, about 160 mg/mL, about 180 mg/mL, about 200 mg/mL, about 220 mg/mL, or about 250 mg/mL. In certain embodiments, the concentration of furosemide in the unit liquid pharmaceutical formulation is about 100 mg/mL.

In various embodiments, the pH of the unit liquid pharmaceutical formulations described herein can be from about 5.5 to about 8.5, from about 6 to about 8.5, from about 6.5 to about 8.5, from about 7 to about 8.5, from about 7.5 to about 8.5, from about 8 to about 8.5, from about 5.5 to about 8, from about 5.5 to about 7.5, from about 5.5 to about 7, from about 5.5 to about 6.5, from about 5.5 to about 6, from about 6 to about 8, from about 6 to about 7.5, from about 6 to about 7, from about 6 to about 6.5, from about 6.5 to about 8, from about 6.5 to about 7.5, from about 6.5 to about 7, from about 7 to about 8, from about 7 to about 7.5, or from about 7.5 to about 8. In certain embodiments, the pH of the unit liquid pharmaceutical formulation is from about 6.5 to about 8.5. In certain embodiments, the pH of the unit liquid pharmaceutical formulation is from about 7 to about 8. In certain embodiments, the pH of the unit liquid pharmaceutical formulation is from about 5.5 to about 6.5.

In various embodiments, the pH of the unit liquid pharmaceutical formulations described herein can be about 5.5, about 6, about 6.5, about 7, about 7.5, about 8, or about 8.5. In certain embodiments, the pH of the unit liquid pharmaceutical formulation is about 7.4.

In various embodiments, the pH of the unit liquid pharmaceutical formulations described herein can be 5.5±0.1, 6±0.1, 6.5±0.1, 7±0.1, 7.5±0.1, 8±0.1, or 8.5±0.1. In certain embodiments, the pH of the unit liquid pharmaceutical formulation is about 7.4±0.1.

In various embodiments, a unit liquid pharmaceutical formulation comprises:
  (i) from about 10 mg to about 200 mg furosemide, or a pharmaceutically acceptable salt thereof;
  (ii) from about 0.1% (w/w) to about 10% (w/w) benzyl alcohol; and
  (iii) from about 25 mM to about 250 mM tromethamine or a pharmaceutically acceptable salt thereof,
wherein the concentration of furosemide in the unit liquid pharmaceutical formulation is from about 5 mg/mL to about 100 mg/mL and the pH of the unit liquid pharmaceutical formulation is about from about 5.5 to about 6.5.

In various embodiments, a unit liquid pharmaceutical formulation comprises:
  (i) from about 10 mg to about 200 mg furosemide, or a pharmaceutically acceptable salt thereof;
  (ii) from about 0.1% (w/w) to about 10% (w/w) N-methyl-pyrrolidone;
  (iii) from about 0.1% (w/w) to about 10% (w/w) benzyl alcohol; and
  (iv) from about 25 mM to about 250 mM tromethamine or a pharmaceutically acceptable salt thereof,
wherein the concentration of furosemide in the unit liquid pharmaceutical formulation is from about 5 mg/mL to about 100 mg/mL and the pH of the unit liquid pharmaceutical formulation is about from about 5.5 to about 6.5.

In various embodiments, a liquid pharmaceutical formulation comprises:
  (i) from about 10 mg to about 200 mg furosemide, or a pharmaceutically acceptable salt thereof;
  (ii) from about 1% (w/w) to about 25% (w/w) N-methyl-pyrrolidone;
  (iii) from about 0.5% (w/w) to about 5% (w/w) benzyl alcohol; and
  (iv) from about 25 mM to about 250 mM tromethamine or a pharmaceutically acceptable salt thereof,
wherein the concentration of furosemide in the unit liquid pharmaceutical formulation is from about 5 mg/mL to about 100 mg/mL and the pH of the unit liquid pharmaceutical formulation is about from about 5.5 to about 6.5.

In various embodiments, the concentration of furosemide in the unit liquid pharmaceutical formulations described herein can be from about 5 mg/mL to about 100 mg/mL, from about 10 mg/mL to about 100 mg/mL, from about 5 mg/mL to about 50 mg/mL, from about 5 mg/mL to about 40 mg/mL, from about 5 mg/mL to about 30 mg/mL, from about 5 mg/mL to about 20 mg/mL, from about 5 mg/mL to about 10 mg/mL, from about 10 mg/mL to about 50 mg/mL, from about 10 mg/mL to about 40 mg/mL, from about 10 mg/mL to about 30 mg/mL, from about 10 mg/mL to about 20 mg/mL, from about 20 mg/mL to about 100 mg/mL, from about 30 mg/mL to about 100 mg/mL, from about 40 mg/mL to about 100 mg/mL, from about 50 mg/mL to about 100 mg/mL, from about 20 mg/mL to about 50 mg/mL, from about 20 mg/mL to about 40 mg/mL, from about 20 mg/mL to about 30 mg/mL, from about 30 mg/mL to about 50 mg/mL, from about 30 mg/mL to about 40 mg/mL, or from about 40 mg/mL to about 50 mg/mL. In certain embodiments, the concentration of furosemide in the unit liquid pharmaceutical formulation is from about 20 mg/mL to about 100 mg/mL. In certain embodiments, the concentration of furosemide in the unit liquid pharmaceutical formulation is from about 5 mg/mL to about 20 mg/mL.

In various embodiments, the concentration of furosemide in the unit liquid pharmaceutical formulations described herein can be greater than about 5 mg/mL, greater than about 10 mg/mL, greater than about 20 mg/mL, greater than about 30 mg/mL, greater than about 40 mg/mL, greater than about 50 mg/mL, greater than about 60 mg/mL, greater than about 70 mg/mL, greater than about 80 mg/mL, greater than about 90 mg/mL, or greater than about 100 mg/mL. In certain embodiments, the concentration of furosemide in the unit liquid pharmaceutical formulation is greater than about 5 mg/mL. In certain embodiments, the concentration of furosemide in the unit liquid pharmaceutical formulation is greater than about 20 mg/mL.

In various embodiments, the concentration of furosemide in the unit liquid pharmaceutical formulations described herein can be about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL.

In various embodiments, the unit liquid pharmaceutical formulations described herein further comprise a pharmaceutically acceptable pH adjuster. In certain embodiments, the pharmaceutically acceptable pH adjuster is selected from the group consisting of acetic acid, citric acid, fumaric acid, hydrochloric acid, malic acid, nitric acid, phosphoric acid, propionic acid, sulfuric acid, tartaric acid, ammonia solution, ammonium carbonate, diethanolamine, potassium hydroxide, sodium bicarbonate, sodium borate, sodium carbonate, sodium hydroxide or trolamine. In certain embodiments, the pharmaceutically acceptable pH adjuster is sodium hydroxide or hydrochloric acid.

In various embodiments, the unit liquid pharmaceutical formulations described herein further comprise an osmolarity adjuster. In certain embodiments, the osmolarity adjuster is selected from the group comprising sodium chloride, potassium chloride, isosorbide, mannitol, xylitol or any combination thereof. In certain embodiments, the osmolarity adjuster is sodium chloride.

In various embodiments, the unit liquid pharmaceutical formulations described herein may further comprise one or more additional pharmaceutically acceptable carriers, excipients, or diluents. Examples of liquid carriers for parenteral administration include water, alcohols (including monohydric alcohols and polyhydric alcohols, e.g., glycols) and their derivatives, and oils (e.g., fractionated coconut oil and *arachis* oil). Examples of such carriers are well known to those skilled in the art and can be prepared in accordance with acceptable pharmaceutical procedures, such as, for example, those described in *Remington: The Science and Practice of Pharmacy*, 20th edition, ed. Alfonso R. Gennaro (Lippincott Williams & Wilkins, Baltimore, Md. (2000)). For example, liquid media or liquid carriers (which are used interchangeably herein) can be used in preparing the liquid pharmaceutical formulations described herein such as solutions, suspensions, and emulsions.

In certain embodiments, the unit liquid pharmaceutical formulation comprises one of more of water; a pH adjuster; and an osmolarity adjuster. In particular embodiments, the pH adjuster is selected from the group consisting of potassium hydroxide, sodium hydroxide, hydrochloric acid, and combinations thereof. In some embodiments, the osmolarity adjuster is selected from the group consisting of sodium chloride, potassium chloride, and combinations thereof.

In various embodiments, the unit liquid pharmaceutical formulations described herein may further comprise other suitable pharmaceutically acceptable additives such as solubilizers, emulsifiers, buffers, preservatives, sweeteners, flavoring agents, suspending agents, thickening agents, colors, viscosity regulators, stabilizers, and osmo-regulators.

In various embodiments, the unit liquid pharmaceutical formulations described herein further comprise a second therapeutic agent. In certain embodiments, furosemide is the sole therapeutic agent present in the unit liquid pharmaceutical formulations described herein.

In various embodiments, the unit liquid pharmaceutical formulations described herein can have an osmolarity in the range of from about 100 mOsm/kg to about 1600 mOsm/kg, from about 200 mOsm/kg to about 1600 mOsm/kg, from about 400 mOsm/kg to about 1600 mOsm/kg, from about 800 mOsm/kg to about 1600 mOsm/kg, from about 1200 mOsm/kg to about 1600 mOsm/kg, from about 100 mOsm/kg to about 1200 mOsm/kg, from about 100 mOsm/kg to about 800 mOsm/kg, from about 100 mOsm/kg to about 400 mOsm/kg, from about 100 mOsm/kg to about 200 mOsm/kg, from about 200 mOsm/kg to about 1200 mOsm/kg, from about 200 mOsm/kg to about 800 mOsm/kg, from about 200 mOsm/kg to about 400 mOsm/kg, from about 400 mOsm/kg to about 1200 mOsm/kg, from about 400 mOsm/kg to about 800 mOsm/kg, or from about 800 mOsm/kg to about 1200 mOsm/kg. In some embodiments, the unit liquid pharmaceutical formulations described herein have an osmolarity in the range of from about 200 mOsm/kg to about 400 mOsm/kg.

In various embodiments, the unit liquid pharmaceutical formulations described herein can have an osmolarity in the range of from about 275 mOsm/kg to about 350 mOsm/kg. In certain embodiments, the unit liquid pharmaceutical formulations described herein are isosmotic.

In various embodiments, the unit liquid pharmaceutical formulations described herein have a volume of from about 0.05 mL to about 40 mL, from about 0.1 mL to about 40 mL, from about 0.5 mL to about 40 mL, from about 1 mL to about 40 mL, from about 2 mL to about 40 mL, from about 5 mL to about 40 mL, from about 10 mL to about 40 mL, from about 20 mL to about 40 mL, from about 0.05 mL to about 20 mL, from about 0.05 mL to about 10 mL, from about 0.05 mL to about 5 mL, from about 0.05 mL to about 2 mL, from about 0.05 mL to about 1 mL, from about 0.05 mL to about 0.5 mL, from about 0.05 mL to about 0.1 mL, from about 0.1 mL to about 20 mL, from about 0.1 mL to about 10 mL, from about 0.1 mL to about 5 mL, from about 0.1 mL to about 2 mL, from about 0.1 mL to about 1 mL, from about 0.1 mL to about 0.5 mL, from about 0.5 mL to about 20 mL, from about 0.5 mL to about 10 mL, from about 0.5 mL to about 5 mL, from about 0.5 mL to about 2 mL, from about 0.5 mL to about 1 mL, from about 1 mL to about 20 mL, from about 1 mL to about 10 mL, from about 1 mL to about 5 mL, from about 1 mL to about 2 mL, from about 2 mL to about 20 mL, from about 2 mL to about 10 mL, from about 2 mL to about 5 mL, from about 5 mL to about 20 mL, from about 5 mL to about 10 mL, or from about 10 mL to about 20 mL. In certain embodiments, the unit liquid pharmaceutical formulations described herein have a volume of from about 0.5 mL to about 20 mL. In certain embodiments, the unit liquid pharmaceutical formulations described herein have a volume of from about 0.5 mL to about 10 mL.

In various embodiments, the unit liquid pharmaceutical formulations described herein have a volume of about 0.05 mL, about 0.1 mL, about 0.5 mL, about 1 mL, about 1.5 mL, about 2 mL, about 2.5 mL, about 3 mL, about 3.5 mL, about 4 mL, about 4.5 mL, about 5 mL, about 6 mL, about 7 mL, about 8 mL, about 9 mL, about 10 mL, about 20 mL, or about 40 mL. In certain embodiments, the unit liquid pharmaceutical formulations described herein have a volume of about 3.5 mL or about 10 mL.

Methods of Treatment

In one aspect, the liquid pharmaceutical formulations or unit liquid pharmaceutical formulations described herein may be used for the treatment or prevention of a variety of diseases and disorders such as, but not limited to, congestion, edema, fluid overload, or hypertension in a patient in need thereof.

In various embodiments, the method comprises administering to the patient a liquid pharmaceutical formulation described herein, wherein the liquid pharmaceutical formulation generally comprises:
 (i) furosemide, or a pharmaceutically acceptable salt thereof;
 (ii) one or more pharmaceutically acceptable excipients; and
 (iii) a pharmaceutically acceptable buffer,
wherein the concentration of furosemide in the liquid pharmaceutical formulation is from about 40 mg/mL to about 250 mg/mL. In certain embodiments, the pH of the liquid pharmaceutical formulation is from about 6.5 to about 8.5.

In various embodiments, the method comprises administering to the patient a unit liquid pharmaceutical formulation described herein, wherein the unit liquid pharmaceutical formulation generally comprises:
 (i) from about 10 mg to about 200 mg furosemide, or a pharmaceutically acceptable salt thereof;
 (ii) one or more pharmaceutically acceptable excipients; and
 (iii) a pharmaceutically acceptable buffer.
wherein the concentration of furosemide in the unit liquid pharmaceutical formulation is from about 40 mg/mL to about 200 mg/mL. In certain embodiments, the pH of the unit liquid pharmaceutical formulation is from about 6.5 to about 8.5.

In certain embodiments, the liquid pharmaceutical formulation further comprises a second therapeutic agent. In some embodiments, the liquid pharmaceutical formulation and the second therapeutic agent are administered simultaneously, together or separately, or separately at different times, as part of a regimen.

In certain embodiments, the liquid pharmaceutical formulations can be administered parenterally, including by infusion, injection or implantation, which includes subcutaneous administration as appropriate. For example, the liquid pharmaceutical formulations can be administered by, for example, subcutaneous injection or delivery, or intravenous injection or delivery. In some embodiments, the liquid pharmaceutical formulation is administered to the patient intravenously. In some embodiments, the liquid pharmaceutical formulation is administered to the patient by subcutaneous injection or subcutaneous infusion. In some embodiments, the liquid pharmaceutical formulation is administered to the patient by subcutaneous infusion using an on-body, subcutaneous delivery system. In some embodiments, the liquid pharmaceutical formulation is administered to the patient by subcutaneous infusion using a wearable subcutaneous delivery system. In some embodiments, the liquid pharmaceutical formulation is administered to the patient by subcutaneous infusion using a pump device. In some embodiments, the pump device is a micropump device or a patch device. In some embodiments, the pump device is a patch device.

In certain embodiments, the liquid pharmaceutical formulation is administered to the patient by subcutaneous infusion over about 0.5 hrs, about 1.0 hrs, about 1.5 hrs, about 2.0 hrs, about 4.0 hrs, or about 8.0 hrs.

In certain embodiments, the unit liquid pharmaceutical formulation further comprises a second therapeutic agent. In some embodiments, the unit liquid pharmaceutical formulation and the second therapeutic agent are administered simultaneously, together or separately, or separately at different times, as part of a regimen.

In certain embodiments, the unit liquid pharmaceutical formulations can be administered parenterally, including by infusion, injection or implantation, which includes subcutaneous administration as appropriate. For example, the unit liquid pharmaceutical formulations can be administered by, for example, subcutaneous injection or delivery, or intravenous injection or delivery. In some embodiments, the unit liquid pharmaceutical formulation is administered to the patient intravenously. In some embodiments, the unit liquid pharmaceutical formulation is administered to the patient by subcutaneous injection or subcutaneous infusion. In some embodiments, the unit liquid pharmaceutical formulation is administered to the patient by subcutaneous infusion using an on-body, subcutaneous delivery system. In some embodiments, the unit liquid pharmaceutical formulation is administered to the patient by subcutaneous infusion using a wearable subcutaneous delivery system. In certain embodiments, the unit liquid pharmaceutical formulation is administered to the patient by subcutaneous infusion using a pump device. In some embodiments, the pump device is a micropump device or a patch device. In some embodiments, the pump device is a patch device.

In certain embodiments, the unit liquid pharmaceutical formulation is administered to the patient by subcutaneous infusion over about 0.5 hrs, about 1 hrs, about 1.5 hrs, about 2 hrs, about 4 hrs, or about 8 hrs.

When administered for the treatment or prevention of a disease or disorder disclosed herein, it may be understood that an effective dosage can vary depending upon many factors such as the particular compound or therapeutic combination utilized, the mode of administration, and severity of the condition being treated, as well as the various physical factors related to the individual being treated. In therapeutic applications, a liquid pharmaceutical formulation or unit liquid pharmaceutical formulation described herein may be provided to a patient already suffering from said disease or disorder in an amount sufficient to cure or at least partially ameliorate the symptoms of the disease or disorder and its complications. The dosage to be used in the treatment of a specific individual typically must be subjectively determined by an attending physician. The variables involved include the specific condition and state as well as the size, age and response pattern of the patient. In some embodiments, the amount sufficient to cure or at least partially ameliorate the symptoms of the disease or disorder and its complications is an effective amount. In some embodiments, the amount sufficient to cure or at least partially ameliorate the symptoms of the disease or disorder and its complications is a therapeutically effective amount.

Kits

In one aspect, the invention provides kits for the treatment or prevention of a variety of diseases and disorders such as, but not limited to, congestion, edema, fluid overload, or hypertension in a patient in need thereof.

In various embodiments, a kit comprises a liquid pharmaceutical formulation described herein. In certain embodiments, the kit comprises one or more unit doses of the liquid pharmaceutical formulation. In certain embodiments, the kit further comprises a medical device. In certain embodiments, the kit further comprises instructions for treating a disease or disorder of the present invention.

In various embodiments, a kit comprises a unit liquid pharmaceutical formulation described herein. In certain embodiments, the kit comprises one or more units of the liquid pharmaceutical formulation. In some embodiments, the kit comprises one, two, three or more units of the liquid pharmaceutical formulation. In certain embodiments, the kit further comprises a medical device. In certain embodiments, the kit further comprises instructions for treating a disease or disorder of the present invention.

A number of medical devices have been proposed to facilitate self-administration of a pharmaceutical formulation. The device may include a reservoir containing, for example, pre-loaded with, the liquid pharmaceutical formulation described herein to be administered. For example, a micropump can provide precise subcutaneous administration of small quantities of a liquid pharmaceutical formulation. Such micropumps can be compact and portable. Another type of device useful for subcutaneous delivery or administration of pharmaceutical formulations is often referred to as a patch device, an on-body, subcutaneous delivery system, or a wearable subcutaneous delivery system (e.g., a pump-patch device). Patch devices usually are attached directly to the skin of a patient.

Accordingly, in various embodiments, a medical device such as a micropump or patch device can include a reservoir containing a pharmaceutical formulation, a subcutaneous injection needle configured for removable insertion into skin of a patient, a micropump having an inlet in fluid communication with the reservoir and an outlet in fluid communication with the subcutaneous injection needle, a control system configured for controlling the micropump to deliver the pharmaceutical formulation from the reservoir to the subcutaneous injection needle, whereby the pharmaceutical formulation is administered subcutaneously to a patient, and a housing for supporting the reservoir, subcutaneous injection needle, micropump and control system, the housing being portable and adapted for contact with the skin of the patient. The liquid pharmaceutical formulation contained within the reservoir can be any of the liquid pharmaceutical formulations or the unit liquid pharmaceutical formulations described herein.

In certain embodiments, the medical device can be of a unitary construction. Such medical devices can be for a single or one-time use. In particular embodiments, the medical device can be of a multi-piece construction. In such medical devices, a disposable or a reusable portion or component can be present. For example, a housing defining or including the reservoir can be a disposable or a reusable component of the medical device. In some embodiments, the disposable or reusable housing defining or including the reservoir can contain a pharmaceutical formulation of the present teachings. In various embodiments, the subcutaneous injection needle can be a disposable component of the medical device.

In certain embodiments, the medical device is a pump device. In some embodiments, the pump device is a micropump device or a patch device. In some embodiments, the pump device is a patch device. In certain embodiments, the medical device is selected from the group comprising a needle and syringe set, an autoinjector, a single use fixed dose injection pen, a multiuse fixed dose injection pen, a single use variable dose injection pen, or a multiuse variable dose injection pen.

EXAMPLES

The invention now being generally described, will be more readily understood by reference to the following examples, which are merely for the purposes of illustration of certain aspects and embodiments of the present invention, and are not intended to limit the invention.

Example 1. Effect of pH on Furosemide Solubility in Liquid Pharmaceutical Formulations The solubility of furosemide was determined in six buffers over a pH-range of pH=6.0-8.5 at two buffer strengths (50 and 200 mM). The tested buffers are found Table 1.

TABLE 1

Buffer Composition for pH Solubility Studies

| Screening Round # | Buffer Strength (mM) | Buffer Type | Target pH |
|---|---|---|---|
| 1 | 50 | Sodium Phosphate | 6.0 |
|   |    |                  | 7.4 |
|   |    |                  | 8.5 |
|   |    | Potassium Phosphate | 6.0 |
|   |    |                  | 7.4 |
|   |    |                  | 8.5 |
|   |    | Tromethamine/HCl | 6.0 |
|   |    |                  | 7.4 |
|   |    |                  | 8.5 |
| 2 | 200 | Histidine/HCl | 6.0 |
|   |    |                  | 7.4 |
|   |    |                  | 8.5 |
|   |    | Citrate* | 6.0 |
|   |    |                  | 7.4 |
|   |    | Tromethamine/HCl | 6.0 |
|   |    |                  | 7.4 |
|   |    |                  | 8.5 |
|   |    | Tromethamine | 6.0 |
|   |    |                  | 7.4 |
|   |    |                  | 8.5 |
|   |    | Sodium Phosphate | 6.0 |
|   |    |                  | 7.4 |
|   |    |                  | 8.5 |
|   |    | Potassium Phosphate | 6.0 |
|   |    |                  | 7.4 |
|   |    |                  | 8.5 |

*A stable pH of 8.5 could not be achieved likely due to lower buffer pKa

Experimental Setup:

Solid furosemide (approx. 100 mg) was added to buffer solutions (2 mL) until the mixture became saturated (approx. 50 mg/mL).

Screening I: pH was adjusted upon preparation and at each time point using base (NaOH, 1 M).

Screening II: Solubility was assisted by sonication (20 min) upon initial preparation and then pH was adjusted (only after sonication) using base (NaOH, 1 M or 12 M).

Samples were tumbled for 48 hours under ambient conditions and protected from light.

At t=2 h, t=24 h, and t=48 h, solids were removed from the samples by centrifugation and the supernatants were tested for appearance, pH, osmolarity, and recovery (HPLC assay).

Results:

The results of the experiments are captured in Table 2 and Table 3.

TABLE 2

Results from Solubility Studies (Screening I)

| Buffer Type | Target pH | Time Point | Average RT [min] | Average Peak Area [mAu] | Apparent pH |
|---|---|---|---|---|---|
| ~50 mM Sodium Phosphate | 6.0 | t2 h | 9.43 | 22197 | 6.10 |
| | | t24 h | 9.62 | 345032 | 6.17 |
| | | t48 h | 9.57 | 336909 | 6.38 |
| | 7.4 | t2 h | 9.42 | 1782711 | 6.90 |
| | | t24 h | 9.40 | 2676432 | 6.90 |
| | | t48 h | 9.58 | 2501189 | 7.01 |
| | 8.5 | t2 h | 9.45 | 2376815 | 6.90 |
| | | t24 h | 9.52 | 3117374 | 6.90 |
| | | t48 h | 9.47 | 3342401 | 7.01 |
| ~50 mM Potassium Phosphate | 6.0 | t2 h | 9.49 | 261577 | 6.10 |
| | | t24 h | 9.50 | 290867 | 6.11 |
| | | t48 h | 9.52 | 256901 | 6.19 |
| | 7.4 | t2 h | 9.45 | 2066328 | 6.80 |
| | | t24 h | 9.55 | 2788914 | 6.95 |
| | | t48 h | 9.60 | 2558554 | 7.04 |
| | 8.5 | t2 h | 9.52 | 3380843 | 6.90 |
| | | t24 h | 9.37 | 4673867 | 7.05 |
| | | t48 h | 9.63 | 3634968 | 7.06 |
| ~50 mM Tromethamine/ HCl | 6.0 | t2 h | 9.60 | 73912 | 6.20 |
| | | t24 h | 9.44 | 219362 | 5.80 |
| | | t48 h | 9.55 | 254334 | 6.07 |
| | 7.4 | t2 h | 9.57 | 1589821 | 6.80 |
| | | t24 h | 9.44 | 2201742 | 6.80 |
| | | t48 h | 9.44 | 1767996 | 6.80 |
| | 8.5 | t2 h | 9.64 | 4080795 | 7.00 |
| | | t24 h | 9.37 | 5061242 | 7.13 |
| | | t48 h | 9.55 | 4359878 | 6.99 |

| Buffer Type | Appearance | Average c(furosemide) [mg/mL] | Stdev [mg/mL] | RSD [%] | Recovery [%]a | Osmolarity [mOsm/Kg] |
|---|---|---|---|---|---|---|
| ~50 mM Sodium Phosphate | Very cloudy | 0.02 | 0.00 | 19.2* | 100 | 212 |
| | Cloudy | 2.70 | 0.24 | 9.0* | 11415 | 118 |
| | Cloudy | 3.06 | 0.63 | 20.5* | 12945 | 141 |
| | Cloudy | 17.17 | 0.71 | 4.1 | 100 | 232 |
| | Cloudy | 25.65 | 1.02 | 4.0 | 149 | 233 |
| | Cloudy | 23.96 | 1.11 | 4.6 | 139 | 237 |
| | Slightly cloudy | 22.76 | 0.62 | 2.7 | 100 | 241 |
| | Slightly cloudy | 29.53 | 0.92 | 3.1 | 130 | 242 |
| | Slightly cloudy | 32.01 | 0.83 | 2.6 | 141 | 276 |
| ~50 mM Potassium Phosphate | Very cloudy | 2.33 | 0.02 | 0.9 | 100 | 108 |
| | Cloudy | 2.77 | 0.09 | 3.2 | 119 | 105 |
| | Cloudy | 2.43 | 0.04 | 1.5 | 104 | 115 |
| | Cloudy | 19.76 | 0.29 | 1.5 | 100 | 193 |
| | Cloudy | 26.73 | 1.00 | 3.7 | 135 | 190 |
| | Cloudy | 24.51 | 0.56 | 2.3 | 124 | 213 |
| | Slightly cloudy | 32.45 | 1.26 | 3.9 | 100 | 265 |
| | Slightly cloudy | 44.94 | 2.88 | 6.4 | 138 | 255 |
| | Slightly cloudy | 40.76 | 0.66 | 1.6 | 126 | 283 |
| ~50 mM Tromethamine/ HCl | Very cloudy | 0.52 | 0.02 | 3.0 | 100 | 124 |
| | Cloudy | 1.92 | 0.04 | 2.2 | 371 | 129 |
| | Cloudy | 2.37 | 0.10 | 4.3 | 457 | 133 |
| | Cloudy | 15.16 | 0.30 | 2.0 | 100 | 165 |
| | Cloudy | 21.07 | 0.28 | 1.3 | 139 | 181 |
| | Cloudy | 16.88 | 1.59 | 9.4 | 111 | 186 |
| | Slightly cloudy | 39.21 | 0.99 | 2.5 | 100 | 242 |

TABLE 2-continued

| | Results from Solubility Studies (Screening I) | | | | |
|---|---|---|---|---|---|
| Slightly cloudy | 48.68 | 1.76 | 3.6 | 124 | 239 |
| Slightly cloudy | 44.24 | 3.78 | 8.5 | 113 | 258 | aRecovery [%]= set to 100 for $t_{2\ h}$.
*Measurement obtained from duplicate analysis.

TABLE 3

Results from Solubility Studies (Screening II)

| Buffer Type | Target pH | Time Point | Average RT [min] | Average Peak Area [mAu] | Apparent pH |
|---|---|---|---|---|---|
| 200 mM Histidine/HCl | 6.0 | t2 h | 11.82 | 374540 | 6.1 |
| | | t24 h | 11.39 | 191961 | 6.2 |
| | | t48 h | 11.42 | 173725 | 6.2 |
| | 7.4 | t2 h | 11.61 | 2284085 | 7.6 |
| | | t24 h | 11.41 | 1917826 | 7.6 |
| | | t48 h | 11.42 | 957586 | 7.6 |
| | 8.5 | t2 h | 11.63 | 1789646 | 8.6 |
| | | t24 h | 11.42 | 1615857 | 8.6 |
| | | t48 h | 11.42 | 871724 | 8.6 |
| 200 mM Citrate | 6.0 | t2 h | 11.76 | 426896 | 6.1 |
| | | t24 h | 11.41 | 119426 | 6.1 |
| | | t48 h | 11.44 | 86361 | 6.1 |
| | 7.4 | t2 h | 11.67 | 1063430 | 7.6 |
| | | t24 h | 11.38 | 691059 | 7.4 |
| | | t48 h | 11.42 | 388579 | 7.4 |
| 200 mM Tromethamine/HCl | 6.0 | t2 h | 11.75 | 626638 | 6.1 |
| | | t24 h | 11.42 | 194823 | 6.1 |
| | | t48 h | 11.42 | 231207 | 6.2 |
| | 7.4 | t2 h | 11.72 | 2552568 | 7.0 |
| | | t24 h | 11.43 | 2020974 | 7.0 |
| | | t48 h | 11.42 | 2025794 | 7.0 |
| | 8.5 | t2 h | 11.71 | 4020943 | 8.8 |
| | | t24 h | 11.44 | 3021911 | 8.3 |
| | | t48 h | 11.43 | 2009714 | 8.6 |
| 200 mM Tromethamine | 6.0 | t2 h | 11.93 | 1279330 | 6.1 |
| | | t24 h | 11.44 | 217301 | 6.3 |
| | | t48 h | 11.44 | 215822 | 6.2 |
| | 7.4 | t2 h | 11.82 | 3578860 | 7.6 |
| | | t24 h | 11.44 | 2711852 | 7.6 |
| | | t48 h | 11.43 | 2717488 | 7.6 |
| | 8.5 | t2 h | 11.83 | 3258887 | 8.7 |
| | | t24 h | 11.43 | 2736373 | 8.7 |
| | | t48 h | 11.43 | 2770650 | 8.7 |
| 200 mM Sodium Phosphate | 6.0 | t2 h | 11.44 | 110543 | 5.9 |
| | | t24 h | 11.42 | 134417 | 5.9 |
| | | t48 h | 11.42 | 144645 | 6.2 |
| | 7.4 | t2 h | 11.43 | 629428 | 7.5 |
| | | t24 h | 11.43 | 733746 | 7.2 |
| | | t48h | 11.42 | 957966 | 7.3 |
| | 8.5 | t2 h | 11.41 | 586353 | 8.6 |
| | | t24 h | 11.43 | 694568 | 8.6 |
| | | t48 h | 11.42 | 964511 | 8.4 |
| 200 mM Potassium Phosphate | 6.0 | t2 h | 11.42 | 110247 | 5.8 |
| | | t24 h | 11.42 | 120065 | 6.2 |
| | | t48 h | 11.41 | 136073* | 6.1 |
| | 7.4 | t2 h | 11.43 | 1255655 | 7.2 |
| | | t24 h | 11.42 | 1749176 | 7.4 |
| | | t48 h | 11.42 | 2255569 | 7.4 |
| | 8.5 | t2 h | 11.41 | 1082568 | 8.4 |
| | | t24 h | 11.42 | 1492050 | 8.6 |
| | | t48 h | 11.41 | 2085497 | 8.7 |

| Buffer Type | Appearance | Average c(furosemide) [mg/mL] | Stdev [mg/mL] | % RSD | Recovery [%]a | Osmolarity [mOsm/kg] |
|---|---|---|---|---|---|---|
| 200 mM Histidine/HCl | Very Cloudy | BLQ | NA | NA | NA | 441 |
| | Very Cloudy | 2.81 | 0.02 | 0.7 | NA | 392 |
| | Very Cloudy | 2.54 | 0.00 | 0.1 | NA | 477 |
| | Cloudy | 25.49 | 0.61 | 2.4 | 100 | 588 |

TABLE 3-continued

Results from Solubility Studies (Screening II)

| | | | | | | |
|---|---|---|---|---|---|---|
| | Cloudy | 28.42 | 0.07 | 0.2 | 111 | 584 |
| | Cloudy | 14.14 | 0.05 | 0.4 | 55 | 616 |
| | Slightly Cloudy | 18.76 | 0.15 | 0.8 | 100 | 553 |
| | Slightly Cloudy | 23.94 | 0.12 | 0.5 | 128 | 558 |
| | Cloudy | 12.87 | 0.03 | 0.2 | 69 | 678 |
| 200 mM Citrate | Very Cloudy | 0.21 | 0.01 | 2.9 | 100 | 516 |
| | Very Cloudy | 1.74 | 0.01 | 0.7 | 829 | 533 |
| | Very Cloudy | 1.25 | 0.00 | 0.1 | 595 | 557 |
| | Cloudy | 8.89 | 0.11 | 1.2 | 100 | 488 |
| | Cloudy | 10.22 | 0.03 | 0.3 | 115 | 484 |
| | Cloudy | 5.73 | 0.03 | 0.5 | 64 | 549 |
| 200 mM Tromethamine/ HCl | Very Cloudy | 2.62 | 0.11 | 4.4 | 100 | 121 |
| | Very Cloudy | 2.86 | 0.00 | 0.2 | 109 | 114 |
| | Very Cloudy | 3.47 | 0.01 | 0.2 | 132 | 127 |
| | Cloudy | 29.14 | 0.27 | 0.9 | 100 | 232 |
| | Cloudy | 29.95 | 0.11 | 0.4 | 103 | 215 |
| | Cloudy | 29.85 | 0.10 | 0.2 | 102 | 233 |
| | Slightly Cloudy | 50.92 | 2.44 | 7.3 | 100 | 177 |
| | Slightly Cloudy | 44.80 | 0.07 | 0.2 | 88 | 257 |
| | Cloudy | 29.61 | 0.54 | 0.2 | 58 | 252 |
| 200 mM Tromethamine | Very Cloudy | 11.93 | 0.05 | 0.4 | 100 | 403 |
| | Very Cloudy | 3.19 | 0.02 | 0.5 | 27 | 406 |
| | Very Cloudy | 3.24 | 0.00 | 0.1 | 27 | 446 |
| | Slightly Cloudy | 43.09 | 1.99 | 4.6 | 100 | 434 |
| | Slightly Cloudy | 40.20 | 0.08 | 0.2 | 93 | 481 |
| | Slightly Cloudy | 40.01 | 0.11 | 0.3 | 93 | 482 |
| | Slightly Cloudy | 38.89 | 0.16 | 0.4 | 100 | 403 |
| | Slightly Cloudy | 40.56 | 0.07 | 0.2 | 104 | 347 |
| | Slightly Cloudy | 40.79 | 0.66 | 1.6 | 105 | 433 |
| 200 mM Sodium Phosphate | Very Cloudy | 1.70 | 0.02 | 0.9 | 100 | 388 |
| | Very Cloudy | 2.00 | 0.04 | 2.0 | 118 | 399 |
| | Cloudy | 2.15 | 0.02 | 1.0 | 126 | 393 |
| | Cloudy | 9.32 | 0.13 | 1.4 | 100 | 330 |
| | Cloudy | 10.79 | 0.16 | 1.5 | 116 | 310 |
| | Slightly Cloudy | 14.08 | 0.08 | 0.5 | 151 | 310 |
| | Cloudy | 8.69 | 0.08 | 1.0 | 100 | 282 |
| | Cloudy | 10.21 | 0.04 | 0.4 | 117 | 267 |
| | Slightly Cloudy | 14.17 | 0.25 | 1.7 | 163 | 285 |
| 200 mM Potassium Phosphate | Very Cloudy | 1.69 | 0.02 | 1.0 | 100 | 384 |
| | Very Cloudy | 1.79 | 0.01 | 0.3 | 106 | 383 |
| | Cloudy | 2.02* | 0.04* | 1.86* | 120* | 376 |
| | Cloudy | 18.53 | 0.05 | 0.3 | 100 | 462 |
| | Cloudy | 25.68 | 0.23 | 0.9 | 139 | 471 |
| | Slightly Cloudy | 33.11 | 0.23 | 0.7 | 179 | 481 |
| | Cloudy | 15.98 | 0.09 | 0.6 | 100 | 487 |
| | Cloudy | 21.91 | 0.45 | 2.0 | 137 | 497 |
| | Slightly Cloudy | 30.62 | 0.45 | 1.5 | 192 | 423 | aRecovery [%] = set to 100 for $t_{2\,h}$.
*Measurement obtained from duplicate analysis.
BLQ = Below the limit of quantification.

Solubilities were determined to be dependent on buffer type (at higher buffer strengths) and were observed to increase at increasing pH values.

pH Screening Round I

The solubility of furosemide was initially determined in sodium phosphate, potassium phosphate, and tromethamine/HCl buffers at a concentration of 50 mM.

A significant pH shift was observed for test samples at pH>7.4 over the course of 48 h due to the API. This shift was observed at each time point indicating slow dissolution rates of furosemide in the buffer media.

Maximum equilibrium solubilities could not be determined for pH 7.4 and 8.5 due to the pH being shifted to approx. pH=7 (API shift). No pH shifts were observed at pH=6.0.

Generally, solubilities were observed to increase at higher pH values. Furosemide showed highest solubilities of approx. 40 mg/mL. All buffer types appeared to produce similar solubilities.

All samples were observed to be hypotonic, with osmolarity increasing at higher pHs due to increased furosemide solubility.

pH Screening Round II

The pH-solubility of furosemide was determined at an increased buffer strength of 200 mM, in the previous buffers along with Histidine/HCl, Citrate, and Tromethamine over a pH-range of pH=6.0-8.5. Additionally, test samples were sonicated prior to pH adjustment to aid API dissolution and minimize pH shifts throughout the studies.

Only small pH shifts (0.4 pH unit) were observed throughout the studies likely due to the increased buffer strength and the initial sonication that increase dissolution rates.

Super-saturation, likely induced by sonication, was observed at t=2 h and t=24 h for certain buffers.

All test buffers produced low solubilities at pH=6.0 and were shown to support solubilities of 8 mg/mL at higher pHs.

Potassium phosphate appeared to produce higher solubilities (2-fold) than sodium phosphate at higher pHs.

Tromethamine based buffers produced the greatest solubility at higher pHs (approx. 40 mg/mL).

Generally, increasing API concentrations correlated with increasing osmolarity values. Some deviations from this trend are reported for the sodium phosphate test solutions.

Example 2. Effect of Excipients on Furosemide Solubility in Liquid Pharmaceutical Formulations The solubility of Furosemide was determined in vehicles designed to cover a formulation space of excipients (single or mixtures) that are regarded as GRAS/safe and are compatible for subcutaneous administration. Informed by the pH solubility studies, tromethamine was selected as the lead buffer component. A summary overview of the performed screenings is given in Table 4.

TABLE 4

Overview of Excipient Solubility Studies

| Study # | Purpose/Objective |
|---|---|
| 1 | Excipient solubility (48 h)<br>Target c(furosemide) = 100 mg/mL<br>Test solutions: single excipients in neat or aqueous solutions (non-buffered)<br>Excipients: NMP, benzyl alcohol, ethanol, glycerin, PEG 3350, PG, Tween 80, PVP K12, β-cyclodextrin<br>pH = 7.4 |
| 2 | Excipient solubility (48 h)<br>Target c(furosemide) = 100 mg/mL<br>Test solutions: single excipients in neat or aqueous solutions (non-buffered and no pH-adjustment)<br>Excipients: NMP, benzyl alcohol, ethanol, glycerin, PEG 3350, PG, Tween 80, PVP K12, β-cyclodextrin |
| 3 | Excipient solubility (48 h)<br>Target c(furosemide) = 100 mg/mL<br>Test solutions: single excipients in buffered solutions<br>Excipients: NMP, benzyl alcohol, ethanol, glycerin, PEG 3350, PG, Tween 80, PVP K12, β-cyclodextrin<br>Buffer strength: 100 mM Tromethamine<br>pH: 7.4 |
| 4 | DOE Full Factorial Study (48 h)<br>Target c(furosemide) = 150 mg/mL<br>Test solutions: excipients (single and mixtures) in buffered solutions<br>Excipients: NMP and benzyl alcohol<br>Buffer strengths: 50 and 100 mM Tromethamine<br>pH: 7.4 |
| 5 | Excipient Solubility (48 h)<br>Target c(furosemide) = 100 mg/mL<br>Test solutions: single excipients in buffered solutions<br>Excipients: NMP, benzyl alcohol, glycerin and PEG 3350<br>Buffer strengths: 100 mM Tromethamine<br>pH: 6.0 |
| 6 | Excipient Solubility (48 h)<br>Target c(furosemide) = 300 mg/mL<br>Test solutions: excipients mixture in buffered solutions<br>Excipients: NMP and benzyl alcohol<br>Buffer strength: 100 mM Tromethamine<br>pH: 4.0, 5.0, 6.0, 7.4 |

Experimental Setup:

Solid furosemide was added to buffer solutions (2 mL) until the mixture became saturated. Solubility was assisted by sonication (20 min) upon initial preparation and then pH was adjusted (only after sonication) using base (NaOH, 12 M).

Samples were tumbled for 48 hours at ambient conditions and protected from light. At t=2 h, t=24 h, and t=48 h, solids were removed from the samples by centrifugation and the supernatants were tested for appearance, pH, osmolarity, and recovery (HPLC assay).

Results

The results of the experiments are captured in Table 5, Table 6, Table 7 and Table 8.

Solubilities for studies I and II could not be determined due to low pHs values and significant pH shifts.

TABLE 5

Results from Excipient Solubility Studies (Study 3)

| Vehicle Composition (pH 7.4) | Time Point | Average RT [min] | Average Peak Area [mAu] | Apparent pH | Appearance |
|---|---|---|---|---|---|
| 100 mM Tromethamine (Control) | t2 h | 11.40 | 1825515 | 7.1 | Cloudy |
| | t24 h | 11.81 | 1786669 | 7.8 | Cloudy |
| | t48 h | 11.82 | 1749022 | 7.6 | Cloudy |
| 100 mM Tromethamine 5% Ethanol | t2 h | 11.41 | 1877232 | 7.5 | Cloudy |
| | t24 h | 11.81 | 1831928 | 7.9 | Cloudy |
| | t48 h | 11.81 | 1818127 | 7.9 | Cloudy |
| 100 mM Tromethamine, 2% Benzyl Alcohol | t2 h | 11.42 | 2718702 | 7.7 | Slightly Cloudy |
| | t24 h | 11.81 | 2698375 | 7.7 | Slightly Cloudy |
| | t48 h | 11.82 | 2681230 | 7.7 | Slightly Cloudy |

TABLE 5-continued

Results from Excipient Solubility Studies (Study 3)

| | | | | | |
|---|---|---|---|---|---|
| 100 mM Tromethamine, 20% Glycerin | t2 h | 11.41 | 2310442 | 7.1 | Cloudy |
| | t24 h | 11.82 | 2266515 | 7.8 | Cloudy |
| | t48 h | 11.83 | 2261250 | 7.8 | Cloudy |
| 100 mM Tromethamine, 20% N-Methyl-pyrrolidone | t2 h | 11.40 | 3029623 | 7.4 | Clear |
| | t24 h | 11.82 | 3128866 | 7.8 | Clear |
| | t48 h | 11.83 | 3108641 | 7.8 | Clear |
| 100 mM Tromethamine, 4% Polyethylene Glycol 3350 | t2 h | 11.40 | 2481519 | 7.4 | Slightly Cloudy |
| | t24 h | 11.81 | 2456383 | 7.9 | Slightly Cloudy |
| | t48 h | 11.82 | 2387681 | 7.5 | Slightly Cloudy |
| 100 mM Tromethamine, 1% Propylene Glycol | t2 h | 11.40 | 2049508 | 7.6 | Cloudy |
| | t24 h | 11.82 | 1962976 | 7.5 | Cloudy |
| | t48 h | 11.82 | 1951402 | 7.8 | Cloudy |
| 100 mM Tromethamine, 0.3% Polysorbate 80 | t2 h | 11.40 | 1900447 | 7.8 | Cloudy |
| | t24 h | 11.81 | 1853124 | 8.1 | Cloudy |
| | t48 h | 11.82 | 1836260 | 7.5 | Cloudy |
| 100 mM Tromethamine, 2% Providone K12 | t2 h | 11.40 | 2230107 | 7.6 | Cloudy |
| | t24 h | 11.81 | 2239373 | 7.9 | Very Cloudy |
| | t48h | 11.83 | 2193443 | 8.0 | Very Cloudy |
| 100 mM Tromethamine, 1% β-Cyclodextrin | t2 h | 11.40 | 2007575 | 7.2 | Cloudy |
| | t24 h | 11.83 | 1967418 | 7.8 | Cloudy |
| | t48 h | 11.82 | 1934515 | 7.6 | Cloudy |

| Vehicle Composition (pH 7.4) | Average c[furosemide] (mg/mL) | Stdev [mg/mL] | RSD [%] | Recovery [%] | Osmolality [mOsm/kg] |
|---|---|---|---|---|---|
| 100 mM Tromethamine (Control) | 53.53 | 0.85 | 1.59 | 100 | 297 |
| | 50.43 | 0.09 | 0.18 | 94 | 272 |
| | 48.93 | 0.29 | 0.59 | 91 | 279 |
| 100 mM Tromethamine 5% Ethanol | 55.07 | 1.15 | 2.1 | 100 | 1163 |
| | 51.72 | 0.43 | 0.8 | 94 | 1173 |
| | 50.87 | 0.45 | 0.9 | 92 | 1159 |
| 100 mM Tromethamine, 2% Benzyl Alcohol | 80.13 | 0.18 | 0.2 | 100 | 454 |
| | 76.32 | 0.23 | 0.3 | 95 | 450 |
| | 75.15 | 0.54 | 0.7 | 94 | 449 |
| 100 mM Tromethamine, 20% Glycerin | 67.97 | 0.49 | 0.7 | 100 | Out of Range |
| | 64.06 | 0.13 | 0.2 | 94 | Out of Range |
| | 63.34 | 0.48 | 0.8 | 93 | Out of Range |
| 100 mM Tromethamine, 20% N-Methyl-pyrrolidone | 89.39 | 0.50 | 0.6 | 100 | Out of Range |
| | 88.54 | 0.97 | 1.1 | 99 | Out of Range |
| | 87.17 | 0.63 | 0.7 | 98 | Out of Range |
| 100 mM Tromethamine, 4% Polyethylene Glycol 3350 | 73.07 | 0.22 | 0.3 | 100 | 404 |
| | 69.45 | 0.09 | 0.1 | 95 | 387 |
| | 66.89 | 0.78 | 1.2 | 92 | 394 |
| 100 mM Tromethamine, 1% Propylene Glycol | 60.20 | 0.24 | 0.4 | 100 | 433 |
| | 55.44 | 0.38 | 0.7 | 92 | 414 |
| | 54.62 | 0.39 | 0.7 | 91 | 421 |
| 100 mM Tromethamine, 0.3% Polysorbate 80 | 55.77 | 1.29 | 2.3 | 100 | 304 |
| | 52.32 | 0.28 | 0.5 | 94 | 334 |
| | 51.38 | 0.98 | 1.9 | 92 | 336 |
| 100 mM Tromethamine, 2% Providone K12 | 65.58 | 0.29 | 0.4 | 100 | 350 |
| | 63.29 | 0.55 | 0.9 | 97 | 307 |
| | 61.43 | 0.70 | 1.1 | 94 | 284 |
| 100 mM Tromethamine, 1% β-Cyclodextrin | 58.96 | 0.19 | 0.3 | 100 | 290 |
| | 55.56 | 0.32 | 0.6 | 94 | 274 |
| | 54.15 | 0.38 | 0.7 | 92 | 278 | aRecovery [%] = set to 100 $t_{2\,h}$.

TABLE 6

Results from Excipient Solubility Studies (Study 4)

| Vehicle Composition (pH 7.4) | Time Point | Average RT [min] | Average Peak Area [mAu] | Apparent pH | Appearance |
|---|---|---|---|---|---|
| 50 mM Tromethamine, 5% NMP | t2 h | 11.39 | 3031917 | 7.4 | Cloudy |
| | t24 h | 11.40 | 2888759 | 7.3 | Cloudy |
| | t48 h | 11.42 | 2787244 | 7.4 | Cloudy |

TABLE 6-continued

Results from Excipient Solubility Studies (Study 4)

| | | | | | |
|---|---|---|---|---|---|
| 50 mM Tromethamine, 20% NMP | t2 h | 11.39 | 4182448 | 7.1 | Clear |
| | t24 h | 11.41 | 4154858 | 7.1 | Clear |
| | t48 h | 11.41 | 4118507 | 6.8 | Clear |
| 50 mM Tromethamine, 5% NMP, 2% Benzyl Alcohol | t2 h | 11.38 | 3728344 | 7.3 | Cloudy |
| | t24 h | 11.41 | 3696317 | 7.3 | Slightly Cloudy |
| | t48 h | 11.42 | 3572812 | 7.3 | Slightly Cloudy |
| 50 mM Tromethamine, 20% NMP, 2% Benzyl Alcohol | t2 h | 11.40 | 4170808 | 7.3 | Clear |
| | t24 h | 11.41 | 4164340 | 7.4 | Clear |
| | t48 h | 11.41 | 4152066 | 7.4 | Clear |
| 100 mM Tromethamine, 5% NMP | t2 h | 11.40 | 3128302 | 7.4 | Cloudy |
| | t24 h | 11.41 | 3118246 | 7.3 | Slightly Cloudy |
| | t48 h | 11.42 | 3006231 | 7.3 | Slightly Cloudy |
| 100 mM Tromethamine, 20% NMP | t2 h | 11.39 | 4130107 | 7.4 | Clear |
| | t24 h | 11.40 | 4116277 | 7.3 | Clear |
| | t48 h | 11.41 | 4112130 | 7.4 | Clear |
| 100 mM Tromethamine, 5% NMP, 2% Benzyl Alcohol | t2h | 11.41 | 4121812 | 7.4 | Clear |
| | t24h | 11.42 | 3969948 | 7.4 | Clear |
| | t48h | 11.41 | 3896373 | 7.4 | Slightly Cloudy |
| 100 mM Tromethamine, 20% NMP, 2% Benzyl Alcohol | t2 h | 11.40 | 4094348 | 7.5 | Clear |
| | t24 h | 11.41 | 4096567 | 7.3 | Clear |
| | t48 h | 11.41 | 4071543 | 7.4 | Clear |
| 75 mM Tromethamine, 12.5% NMP, 1% Benzyl Alcohol | t2 h | 11.40 | 4160110 | 7.4 | Clear |
| | t24 h | 11.42 | 4025902 | 7.4 | Clear |
| | t48 h | 11.41* | 4421340* | 7.4 | Clear |

| Vehicle Composition (pH 7.4) | Average c(furosemide) [mg/mL] | Stdev [mg/mL] | RSD [%] | Recovery [%]a | Osmolality [mOsm/kg] |
|---|---|---|---|---|---|
| 50 mM Tromethamine, 5% NMP | 86.72 | 1.44 | 1.66 | 100 | 706 |
| | 82.58 | 1.10 | 1.33 | 95 | 709 |
| | 79.65 | 1.21 | 1.52 | 92 | 671 |
| 50 mM Tromethamine, 20% NMP | 119.94 | 0.37 | 0.3 | 100 | Out of Range |
| | 119.14 | 0.41 | 0.3 | 99 | Out of Range |
| | 118.09 | 0.25 | 0.2 | 98 | Out of Range |
| 50 mM Tromethamine, 5% NMP, 2% Benzyl Alcohol | 106.83 | 1.80 | 1.7 | 100 | 760 |
| | 105.90 | 0.29 | 0.3 | 99 | 774 |
| | 102.34 | 0.74 | 0.7 | 96 | 782 |
| 50 mM Tromethamine, 20% NMP, 2% Benzyl Alcohol | 119.60 | 2.49 | 2.1 | 100 | Out of Range |
| | 119.42 | 0.85 | 0.7 | 100 | Out of Range |
| | 120.95 | 1.77 | 1.5 | 101 | Out of Range |
| 100 mM Tromethamine, 5% NMP | 89.50 | 2.01 | 2.2 | 100 | 786 |
| | 89.21 | 0.26 | 0.3 | 100 | 752 |
| | 87.42 | 0.58 | 0.7 | 98 | 754 |
| 100 mM Tromethamine, 20% NMP | 118.43 | 0.23 | 0.2 | 100 | Out of Range |
| | 118.03 | 0.92 | 0.8 | 100 | Out of Range |
| | 119.79 | 1.42 | 1.2 | 101 | Out of Range |
| 100 mM Tromethamine, 5% NMP, 2% Benzyl Alcohol | 118.19 | 0.32 | 0.3 | 100 | 848 |
| | 113.80 | 0.58 | 0.5 | 96 | 875 |
| | 113.47 | 0.53 | 0.5 | 96 | 875 |
| 100 mM Tromethamine, 20% NMP, 2% Benzyl Alcohol | 117.40 | 0.24 | 0.2 | 100 | Out of Range |
| | 117.46 | 1.14 | 1.0 | 100 | Out of Range |
| | 118.60 | 0.98 | 0.8 | 101 | Out of Range |
| 75 mM Tromethamine, 12.5% NMP, 1% Benzyl Alcohol | 119.30 | 0.24 | 0.2 | 100 | 1587 |
| | 115.42 | 4.32 | 3.7 | 97 | 1576 |
| | 128.83* | 4.73* | 3.7* | 108* | 1590 | aRecovery [%] = set to 100 for $t_{2\ h}$.
*Measurement obtained from duplicate analysis.

TABLE 7

Results from Excipient Solubility Studies (Study 5)

| Vehicle (pH 6.0) | Time Point | Average RT [min] | Average Peak Area [mAu] | Apparent pH | Appearance |
|---|---|---|---|---|---|
| 100 mM Tromethamine, 2% Benzyl Alcohol | t2 h | 11.41 | 143472 | 6.2 | Very Cloudy |
| | t24 h | 11.42 | 141460 | 5.8 | Very Cloudy |
| | t48 h | 11.39 | 146503 | 5.8 | Very Cloudy |
| 100 mM Tromethamine, 4% PEG 3350 | t2 h | 11.41 | 151028 | 5.9 | Very Cloudy |
| | t24 h | 11.42 | 152347 | 6.1 | Very Cloudy |
| | t48 h | 11.40 | 154068 | 5.8 | Very Cloudy |
| 100 mM Tromethamine, 20% Glycerin | t2 h | 11.42 | 114569 | 6.1 | Very Cloudy |
| | t24 h | 11.41 | 115134 | 6.1 | Very Cloudy |
| | t48 h | 11.40 | 115883 | 5.7 | Very Cloudy |
| 100 mM Tromethamine, 20% NMP | t2 h | 11.42 | 346422 | 6.1 | Very Cloudy |
| | t24 h | 11.42 | 346383 | 6.1 | Very Cloudy |
| | t48 h | 11.39 | 346516 | 5.6 | Very Cloudy |

| Vehicle (pH 6.0) | Average c[furosemide] (mg/mL) | Stdev [mg/mL] | RSD [%] | Recovery [%] | Osmolality [mOsm/kg] |
|---|---|---|---|---|---|
| 100 mM Tromethamine, 2% Benzyl Alcohol | 4.08 | 0.04 | 0.98 | 100 | 393 |
| | 4.06 | 0.03 | 0.77 | 99 | 401 |
| | 4.15 | 0.07 | 1.69 | 102 | 394 |
| 100 mM Tromethamine, 4% PEG 3350 | 4.32 | 0.03 | 0.7 | 100 | 270 |
| | 4.40 | 0.03 | 0.6 | 102 | 272 |
| | 4.38 | 0.01 | 0.2 | 102 | 268 |
| 100 mM Tromethamine, 20% Glycerin | 3.17 | 0.06 | 1.9 | 100 | Out of Range |
| | 3.23 | 0.05 | 1.6 | 102 | Out of Range |
| | 3.18 | 0.05 | 1.6 | 100 | Out of Range |
| 100 mM Tromethamine, 20% NMP | 10.50 | 0.06 | 0.6 | 100 | Out of Range |
| | 10.53 | 0.12 | 1.2 | 100 | Out of Range |
| | 10.48 | 0.06 | 0.6 | 100 | Out of Range | aRecovery [%] = set to 100 for $t_{2\,h}$.

TABLE 8

Results from Excipient Solubility Studies (Study 6)

| Vehicle | Time Point | Average RT [min] | Average Peak Area [mAu] | Apparent pH | Appearance |
|---|---|---|---|---|---|
| 100 mM Tromethamine pH = 4.0, 25% NMP, 2% Benzyl Alcohol | t2 h | 11.43 | 12584 | 3.9 | Very Cloudy |
| | t24 h | 11.41* | 12008* | 3.6 | Very Cloudy |
| | t48 h | 11.42* | 39411* | 4.7 | Very Cloudy |
| 100 mM Tromethamine pH 5.0, 25% NMP, 2% Benzyl Alcohol | t2 h | 11.43 | 59108 | 5.0 | Very Cloudy |
| | t24 h | 11.42 | 57529 | 4.6 | Very Cloudy |
| | t48 h | 11.42 | 92084 | 5.1 | Very Cloudy |
| 100 mM Tromethamine pH 6.0, 25% NMP, 2% Benzyl Alcohol | t2 h | 11.42 | 599711 | 6.0 | Very Cloudy |
| | t24 h | 11.42 | 606643 | 5.8 | Very Cloudy |
| | t48 h | 11.42 | 614155 | 6.1 | Very Cloudy |
| 100 mM Tromethamine pH 7.4, 25% NMP, 2% Benzyl Alcohol | t2 h | 11.43 | 6752752 | 7.3 | Cloudy |
| | t24 h | 11.43 | 7144685 | 7.3 | Cloudy |
| | t48 h | 11.43 | 6669530 | 7.0 | Cloudy |

| Vehicle | Average c(furosemide) [mg/mL] | Stdev [mg/mL] | RSD [%] | Recovery [%] | Osmolality [mOsm/kg] |
|---|---|---|---|---|---|
| 100 mM Tromethamine pH = 4.0, 25% NMP, 2% Benzyl Alcohol | BLQ | NA | NA | NA | Out of Range |
| | BLQ* | NA | NA | NA | Out of Range |
| | 0.75* | 0.09* | 11.8* | NA* | Out of Range |

TABLE 8-continued

Results from Excipient Solubility Studies (Study 6)

| | | | | | |
|---|---|---|---|---|---|
| 100 mM Tromethamine pH 5.0, 25% NMP, 2% Benzyl Alcohol | 1.34 1.35 2.42 | 0.05 0.05 0.02 | 3.5 3.5 0.9 | 100 101 181 | Out of Range Out of Range Out of Range |
| 100 mM Tromethamine pH 6.0, 25% NMP, 2% Benzyl Alcohol | 18.42 18.74 18.94 | 0.09 0.13 0.10 | 0.5 0.7 0.5 | 100 102 103 | Out of Range Out of Range Out of Range |
| 100 mM Tromethamine pH 7.4, 25% NMP, 2% Benzyl Alcohol | 212.77 225.86 210.51 | 1.74 4.37 1.27 | 0.8 1.9 0.6 | 100 106 99 | Out of Range Out of Range Out of Range | aRecovery [%] = set to 100 for $t_{2\,h}$.
*Measurement obtained from duplicate analysis.

Excipient Solubility Studies (Studies 1 and 2)

An attempt was made to determine the solubility of furosemide in non-buffered excipients solutions adjusted to pH of 7.4 using a strong base (NaOH). Solubilities could not be determined due to the pH not being stable upon sample preparation (Study 1).

An attempt was made to determine furosemide solubility in excipients solutions without pH adjustment. All test samples displayed very low solubilities (below the limit of quantification) likely due to the low pHs driven by the API's pKa.

Excipient Solubility Studies (Study 3)

The solubility of furosemide was determined in excipient buffered solutions (tromethamine) at a pH of 7.4. N-methyl-pyrrolidone (NMP, 20%) reported the highest solubility (approx. 87 mg/mL) that was maintained over the course of 48 h. Maximum solubilities could not be determined as saturation was never achieved.

A pH variability (up to 0.7 pH units) was observed for certain conditions throughout the studies.

Benzyl alcohol (BA, 2%), glycerin (20%) and polyethylene glycol (4%) resulted in the highest furosemide solubilities (approx. 60-75 mg/mL) that were maintained over the course of 48 h.

Osmolarities could not be accurately measured due to organic content in some formulations.

Excipient Solubility Studies (Study 4)

A full factorial DOE study was performed to determine the optimal amounts of NMP, benzyl alcohol and buffer (tromethamine) required to produce the highest solubility. Any potential synergistic effects stemming from various excipient combinations were also investigated.

A small pH variability (up to 0.3 pH units) was observed throughout the studies.

Highest solubility (>120 mg/mL) was always achieved at higher NMP concentrations (20%).

Minimum concentrations of 5% NMP in combination with 2% benzyl alcohol were reported to produce a solubility >100 mg/mL.

Furosemide solubility was observed to be highest at high amounts of NMP and BA and was relatively unaffected by buffer strength.

At low NMP levels, higher buffer concentration appeared to produce slightly higher solubilities.

The effect of NMP was stronger at low BA levels and the effect of BA was stronger at low NMP levels. Both are co-solvents and likely dissolve furosemide by the same mechanism.

Osmolarities could not be properly measured due to the organic content of the test vehicles.

Excipient Solubility Studies (Study 5)

The solubility of furosemide was determined in excipient buffered solutions (tromethamine) at pH 6.0.

A small pH variability (up to 0.4 pH units) was observed throughout the studies.

Solubilities ranged from approximately 3-10 mg/mL. N-Methyl-pyrrolidone (20%) yielded the highest solubility (approx. 10 mg/mL) that was maintained over the course of 48 h.

All solutions appeared cloudy indicating saturation of each solution.

Osmolarities could not be properly measured due to the organic content of the test vehicles.

Excipient Solubility Studies (Study 6)

The solubility of furosemide was determined in excipient buffered solutions (N-methyl-pyrrolidone, benzyl alcohol, tromethamine) at pH's 4.0, 5.0, 6.0, and 7.4.

A pH variability of 0.7 units was observed for pH 4.0 test samples.

Solubility significantly increased between pH 6-7.4. The maximum observed solubility of furosemide was approximately 210 mg/mL at pH 7.4.

All solutions appeared cloudy indicating solution saturation. Test samples appeared to increase in viscosity at higher concentrations (around 200 mg/mL).

Osmolarities could not be properly measured due to the organic content of the test vehicles.

Example 3. Manufacturing Process for a Furosemide Liquid Formulation (107 mg/mL Furosemide, 50 mM Tromethamine, 10% (w/v) N-Methyl-Pyrrolidone, 2% (w/v) Benzyl Alcohol)

In the following example, the manufacturing process for preparing a 107 mg/mL furosemide liquid formulation is described.

30.5 g tromethamine (USP), 500.5 g N-methyl-pyrrolidone (USP) and 100.0 g benzyl alcohol (USP) were weighed and added to a 5 L volumetric flask. To this, approximately 2.5 L of ultra-pure water was added and then stirred using a magnetic stirrer bar. Once the solid materials had dissolved 537.5 g furosemide (USP) was added, producing a suspension. After approximately 30 minutes of additional stirring the pH of the suspension/solution was adjusted to 7.4 using a 10N sodium hydroxide solution (~181.0 mL 10N sodium hydroxide solution required). Stirring was continued for a further 30 minutes after which the volume of the solution was made to volume using ultra-pure water. Finally, the pH of the solution was verified and found to be 7.5.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

What is claimed:

1. A liquid pharmaceutical formulation comprising:
   furosemide, or a pharmaceutically acceptable salt thereof, wherein the concentration of furosemide is from about 60 mg/mL to about 200 mg/mL;
   one or more pharmaceutically acceptable excipients, wherein the amount of the one or more pharmaceutically acceptable excipients is from about 0.1% (w/w) to about 30% (w/w); and
   a pharmaceutically acceptable buffer comprising tromethamine or a pharmaceutically acceptable salt thereof, wherein the concentration of tromethamine is from about 25 mM to about 150 mM;
   wherein the liquid pharmaceutical formulation has a pH of between about 6.5 to about 8.5.

2. The liquid pharmaceutical formulation of claim 1, wherein the concentration of furosemide is from about 60 mg/mL to about 120 mg/mL.

3. The liquid pharmaceutical formulation of claim 1, wherein the amount of the one or more pharmaceutically acceptable excipients is from about 0.1% (w/w) to about 10% (w/w).

4. The liquid pharmaceutical formulation of claim 1, wherein the concentration of tromethamine is from about 50 mM to about 125 mM.

5. The liquid pharmaceutical formulation of claim 1, wherein the liquid pharmaceutical formulation has a pH of between about 7 to about 8.5.

6. The liquid pharmaceutical formulation of claim 1, wherein the liquid pharmaceutical formulation has a pH of between about 7 to about 8.

7. The liquid pharmaceutical formulation of claim 1, wherein the one or more pharmaceutically acceptable excipients is selected from the group consisting of ethanol, benzyl alcohol, glycerin, sodium chloride, a polyethylene glycol, propylene glycol, a polysorbate, a polyvinylpyrrolidone, a cyclodextrin, and a combination thereof.

8. The liquid pharmaceutical formulation of claim 1, further comprising one or more of water, an osmolarity adjuster, and a pH adjuster.

9. A liquid pharmaceutical formulation comprising:
   furosemide, or a pharmaceutically acceptable salt thereof, wherein the concentration of furosemide is from about 60 mg/mL to about 120 mg/mL;
   one or more pharmaceutically acceptable excipients, wherein the amount of the one or more pharmaceutically acceptable excipients is from about 0.1% (w/w) to about 10% (w/w); and
   a pharmaceutically acceptable buffer comprising tromethamine or a pharmaceutically acceptable salt thereof, wherein the concentration of tromethamine is from about 25 mM to about 125 mM;
   wherein the liquid pharmaceutical formulation has a pH of between about 7 to about 8.5.

10. The liquid pharmaceutical formulation of claim 9, wherein the concentration of furosemide is about 60 mg/mL to 100 mg/mL.

11. The liquid pharmaceutical formulation of claim 9, wherein the concentration of furosemide is about 70 mg/mL to about 90 mg/mL.

12. The liquid pharmaceutical formulation of claim 9, wherein the liquid pharmaceutical formulation has a pH of between about 7 to about 8.5.

13. The liquid pharmaceutical formulation of claim 9, wherein the one or more pharmaceutically acceptable excipients is selected from the group consisting of ethanol, benzyl alcohol, glycerin, sodium chloride, a polyethylene glycol, propylene glycol, a polysorbate, a polyvinylpyrrolidone, a cyclodextrin, and a combination thereof.

14. The liquid pharmaceutical formulation of claim 9, further comprising one or more of water, an osmolarity adjuster, and a pH adjuster.

15. A liquid pharmaceutical formulation comprising:
   furosemide, or a pharmaceutically acceptable salt thereof, wherein the concentration of furosemide is from about 70 mg/mL to about 100 mg/mL;
   one or more pharmaceutically acceptable excipients, wherein the amount of the one or more pharmaceutically acceptable excipients is from about 0.5% (w/w) to about 5% (w/w); and
   a pharmaceutically acceptable buffer comprising tromethamine or a pharmaceutically acceptable salt thereof, wherein the concentration of tromethamine is from about 25 mM to about 125 mM;
   wherein the liquid pharmaceutical formulation has a pH of between about 7 to about 8.5.

16. The liquid pharmaceutical formulation of claim 15, wherein the concentration of furosemide is about 80 mg/mL.

17. The liquid pharmaceutical formulation of claim 15, wherein the concentration of tromethamine is about 25 mM to 100 mM.

18. The liquid pharmaceutical formulation of claim 17, wherein the liquid pharmaceutical formulation has a pH of between about 7 to about 8.

19. The liquid pharmaceutical formulation of claim 17, wherein the one or more pharmaceutically acceptable excipients is selected from the group consisting of ethanol, benzyl alcohol, glycerin, sodium chloride, a polyethylene glycol, propylene glycol, a polysorbate, a polyvinylpyrrolidone, a cyclodextrin, and a combination thereof.

20. The liquid pharmaceutical formulation of claim 19, further comprising one or more of water, an osmolarity adjuster, and a pH adjuster.

* * * * *